US008998966B2

(12) United States Patent
Yap et al.

(10) Patent No.: US 8,998,966 B2
(45) Date of Patent: Apr. 7, 2015

(54) POLYAXIAL FACET FIXATION SCREW SYSTEM WITH FIXATION AUGMENTATION

(75) Inventors: Marc Yap, The Colony, TX (US); Rob D. Dickerman, Plano, TX (US); Matthew T. Bennett, Vestal, NY (US); Charles R. Forton, Frisco, TX (US); Andrew R. Fauth, River Heights, UT (US); Joel R. Helgerson, Erie, CO (US); Shresta Marigowda, Stratford, CT (US)

(73) Assignee: OsteoMed, LLC, Addison, TX (US)

( * ) Notice: Subject to any disclaimer, the term of this patent is extended or adjusted under 35 U.S.C. 154(b) by 251 days.

(21) Appl. No.: 13/166,638

(22) Filed: Jun. 22, 2011

(65) Prior Publication Data

US 2011/0313472 A1    Dec. 22, 2011

Related U.S. Application Data

(63) Continuation-in-part of application No. 12/957,056, filed on Nov. 30, 2010, now Pat. No. 8,529,609.

(60) Provisional application No. 61/265,614, filed on Dec. 1, 2009, provisional application No. 61/374,862, filed on Aug. 18, 2010, provisional application No. 61/357,273, filed on Jun. 22, 2010.

(51) Int. Cl.
*A61B 17/86* (2006.01)
*A61B 17/70* (2006.01)
*A61B 17/80* (2006.01)
*A61B 17/68* (2006.01)

(52) U.S. Cl.
CPC ......... *A61B 17/7064* (2013.01); *A61B 17/8047* (2013.01); *A61B 17/8625* (2013.01); *A61B 17/686* (2013.01); *A61B 17/8685* (2013.01); *A61B 17/8695* (2013.01); *A61B 2017/8655* (2013.01)

(58) Field of Classification Search
CPC ........... A61B 17/8625; A61B 17/8685; A61B 2017/8655
USPC .................... 606/6–328; 411/21, 22, 358, 359
See application file for complete search history.

(56) References Cited

U.S. PATENT DOCUMENTS

| | | | | |
|---|---|---|---|---|
| 324,768 | A * | 8/1885 | Hunt | 411/358 |
| 958,127 | A * | 5/1910 | Hovrud | 52/160 |
| 1,155,844 | A | 10/1915 | Smith | |
| 1,391,186 | A | 9/1921 | Hill | |
| 1,428,111 | A * | 9/1922 | Molesworth | 411/359 |
| 1,609,645 | A | 12/1926 | DeWire | |
| 1,627,404 | A | 5/1927 | Marcel | |
| 1,792,381 | A | 2/1931 | Paul | |

(Continued)

FOREIGN PATENT DOCUMENTS

| | | |
|---|---|---|
| EP | 0932367 B1 | 11/2003 |
| WO | WO2004019757 | 3/2004 |

(Continued)

*Primary Examiner* — Michael T Schaper
(74) *Attorney, Agent, or Firm* — Norton Rose Fulbright US LLP

(57) ABSTRACT

A screw system includes a screw and a washer assembly captive to the screw. The washer assembly is polyaxially pivotable relative to the screw. The screw may be freely rotated in one direction relative to the washer assembly, but frictionally binds with the washer assembly when rotated in a second direction. Various auxiliary fixation features are disclosed.

18 Claims, 24 Drawing Sheets

(56) References Cited

U.S. PATENT DOCUMENTS

| | | | |
|---|---|---|---|
| 2,583,896 A | 1/1952 | Siebrandt | |
| 2,769,441 A | 11/1956 | Daniel | |
| 3,181,584 A | 5/1965 | Borowsky | |
| 3,865,307 A * | 2/1975 | Schiro | 238/366 |
| 4,290,328 A | 9/1981 | Clark | |
| 5,125,489 A | 6/1992 | Cha | |
| 5,261,909 A | 11/1993 | Sutterlin | |
| 5,478,342 A * | 12/1995 | Kohrs | 606/310 |
| 5,527,312 A | 6/1996 | Ray | |
| 5,556,411 A | 9/1996 | Taoda et al. | |
| 5,611,800 A | 3/1997 | Davis | |
| 5,893,889 A | 4/1999 | Harrington | |
| 5,908,431 A | 6/1999 | Battenfield | |
| 6,148,696 A | 11/2000 | Chiang | |
| 6,227,782 B1 | 5/2001 | Bowling et al. | |
| 6,248,108 B1 | 6/2001 | Tormala et al. | |
| 6,443,987 B1 | 9/2002 | Bryan | |
| 6,485,518 B1 | 11/2002 | Cornwall | |
| 6,502,679 B1 | 1/2003 | Wang | |
| 6,565,573 B1 | 5/2003 | Ferrante | |
| 7,060,068 B2 | 6/2006 | Tromanhauser | |
| 7,261,506 B2 * | 8/2007 | Smolarek | 411/161 |
| 7,294,128 B2 | 11/2007 | Alleyne | |
| 7,396,360 B2 | 7/2008 | Lieberman | |
| 7,522,953 B2 | 4/2009 | Kaula | |
| 7,563,275 B2 | 7/2009 | Falahee | |
| 7,575,343 B2 | 8/2009 | Li | |
| 7,708,761 B2 | 5/2010 | Petersen | |
| 7,824,429 B2 | 11/2010 | Culbert | |
| 8,128,666 B2 * | 3/2012 | Falahee | 606/273 |
| 8,162,942 B2 | 4/2012 | Coati | |
| 2003/0032960 A1 | 2/2003 | Dudasik | |
| 2005/0077688 A1 | 4/2005 | Voegele et al. | |
| 2005/0228386 A1 | 10/2005 | Ziolo et al. | |
| 2006/0074425 A1 | 4/2006 | Sutterlin | |
| 2006/0111779 A1 | 5/2006 | Petersen | |
| 2006/0217713 A1 | 9/2006 | Serhan et al. | |
| 2006/0217715 A1 | 9/2006 | Serhan et al. | |
| 2006/0235391 A1 | 10/2006 | Sutterlin | |
| 2006/0287583 A1 | 12/2006 | Mangiardi | |
| 2008/0021480 A1 | 1/2008 | Chin | |
| 2008/0147079 A1 | 6/2008 | Chin | |
| 2008/0255622 A1 | 10/2008 | Mickiewicz | |
| 2009/0054903 A1 | 2/2009 | Falahee | |
| 2009/0076551 A1 | 3/2009 | Petersen | |
| 2009/0099602 A1 | 4/2009 | Aflatoon | |
| 2009/0192551 A1 | 7/2009 | Cianfrani et al. | |
| 2009/0234397 A1 | 9/2009 | Petersen | |
| 2009/0312798 A1 | 12/2009 | Varela | |
| 2009/0312800 A1 | 12/2009 | Chin | |
| 2010/0174324 A1 * | 7/2010 | Derouet | 606/305 |
| 2010/0222829 A1 | 9/2010 | Petersen | |
| 2011/0087169 A1 | 4/2011 | Parihar et al. | |

FOREIGN PATENT DOCUMENTS

| | | |
|---|---|---|
| WO | WO2006017507 | 2/2006 |
| WO | WO2006057943 | 6/2006 |
| WO | WO-2007/070819 A2 | 6/2007 |
| WO | WO2007084900 | 7/2007 |
| WO | WO2007109402 | 9/2007 |
| WO | WO2007120903 | 10/2007 |
| WO | WO2007127610 | 11/2007 |
| WO | WO2007127687 | 11/2007 |
| WO | WO2007143709 | 12/2007 |
| WO | WO2008086533 | 7/2008 |
| WO | WO2008106240 | 9/2008 |
| WO | WO2008127415 | 10/2008 |
| WO | WO2008127978 | 10/2008 |
| WO | WO2008153732 | 12/2008 |
| WO | WO2009006622 | 1/2009 |
| WO | WO2009067486 | 5/2009 |
| WO | WO-2009/134896 A2 | 11/2009 |
| WO | WO2009134888 | 11/2009 |
| WO | WO-2010/036864 A1 | 4/2010 |

* cited by examiner

POLYAXIAL FACET FIXATION SCREW SYSTEM WITH FIXATION AUGMENTATION

CROSS-REFERENCE TO RELATED APPLICATIONS

This application is a continuation-in-part of:

prior U.S. patent application Ser. No. 12/957,056 filed Nov. 30, 2010, and is entitled "POLYAXIAL FACET FIXATION SCREW SYSTEM".

U.S. patent application Ser. No. 12/957,056 claims the benefit of:

prior U.S. Provisional Patent Application No. 61/265,614 filed Dec. 1, 2009, and is entitled "ANTI-BACK OUT POLYAXIAL FACET FIXATION SCREW SYSTEM"; and prior U.S. Provisional Patent Application No. 61/374,862 filed Aug. 18, 2010, and is entitled "CANNULA INSERTER".

This application also claims the benefit of:

prior U.S. Provisional Patent Application No. 61/357,273 filed Jun. 22, 2010, and is entitled "FACET FIXATION SCREW WITH FIXATION AUGMENTATION".

The above-identified documents are incorporated herein by reference in their entirety.

BACKGROUND

1. Technical Field

The present disclosure relates to orthopedic screw systems for bone fixation, and more particularly, to providing facet joint fixation screw systems with anti-backout features which prevent unintentional withdrawal of the screw.

2. The Relevant Technology

Loosening is a commonly encountered problem with screw fixation. A screw may work its way loose over time, such that fixation is compromised or the screw head protrudes to an undesirable extent from the surrounding material. Loosening is seen in orthopedic applications, such as facet joint fixation or facet joint fusion, at least partially because normal physiologic movement tends to encourage screw migration, and the bone into which the screw is driven tends to remodel over time. The three-dimensional topography of the bone surface presents an additional challenge in achieving secure fixation. The present disclosure provides a low-profile, self-contained, polyaxial, one-way screw and washer system that automatically and continuously resists any tendency of the screw to unthread from the surrounding material.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods used in orthopedic surgery, and in particular, to facet joint fixation. Those of skill in the art will recognize that the systems and methods described herein may be readily adapted for other bone or joint fixation procedures. Those of skill in the art will also recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Figure 1A:
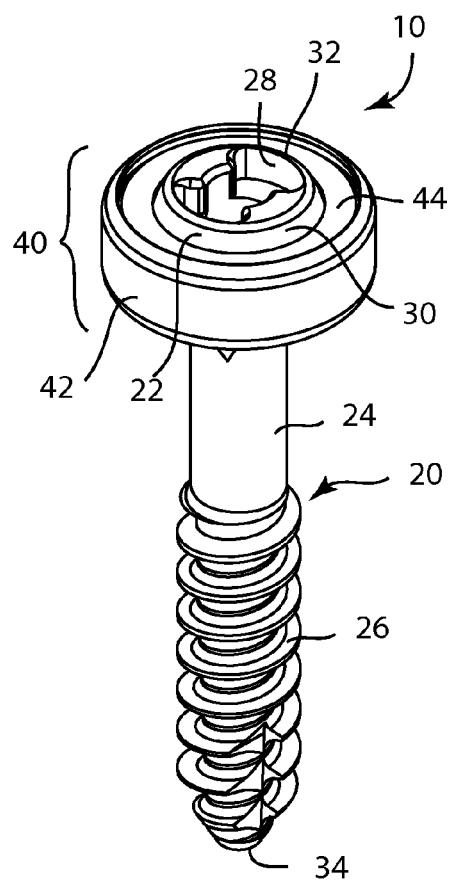
FIG. 1A illustrates a top perspective view of a system including a screw and a washer assembly.
Figure 1B:
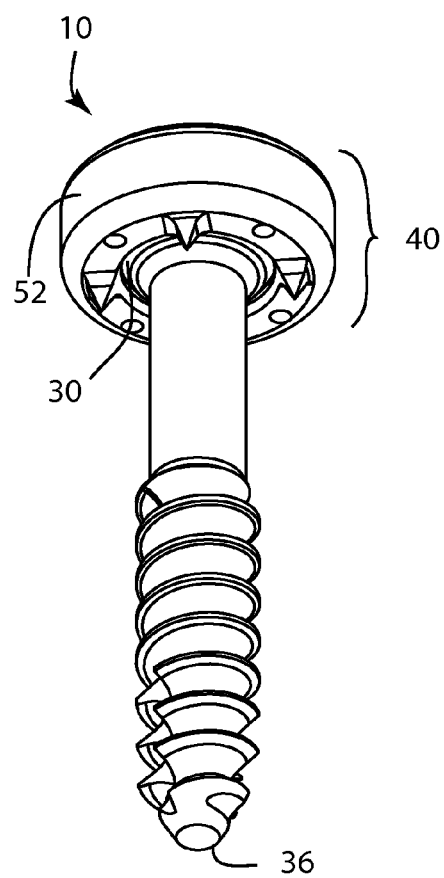
FIG. 1B is a bottom perspective view of the system of FIG. 1A.

Referring to FIGS. 1A and 1B, top and bottom perspective views illustrate a facet fixation screw system 10, comprising a screw 20 and a washer assembly 40. The washer assembly is captive to the head of the screw. The washer assembly includes an anti-backout mechanism which allows the screw to be freely rotated in one direction relative to the washer assembly, but binds the screw to the washer assembly when the screw is rotated in the opposite direction.

Screw 20 includes a spherical head 22 and a shaft 24. The shaft 24 includes a threaded portion 26 extending along a portion of the shaft. The entire length of the shaft may be threaded, or some portion or portions thereof. The thread pitch may be constant along the threaded portion, or may vary. Preferably, the shaft 24 includes a cannulation 25 to allow placement of the screw over a guidewire, but non-cannulated embodiments may also be provided. A drive feature 28 on the head 22 is shaped to cooperate with a driver instrument to facilitate placement, polyaxial adjustment and/or rotational driving of the screw. In the embodiment shown, the drive feature has a dogbone or bowtie shape; however other drive feature shapes are possible, including but not limited to: hexagon, pentagon, square, triangular, rectangular, cross, star, or other driver shapes known in the art. The drive feature 28 may be a recess as shown; in other embodiments the drive feature 28 may protrude to cooperate with a driver instrument having a complementary recessed driving feature. The head 22 further includes a spherical bearing surface 30. The screw 20 further includes a first end 32 which may be a proximal end, and at which the head 22 is located; and a second end 34 which may be a distal end, and at which a tip 36 of the shaft 24 is located.

Figure 4A:
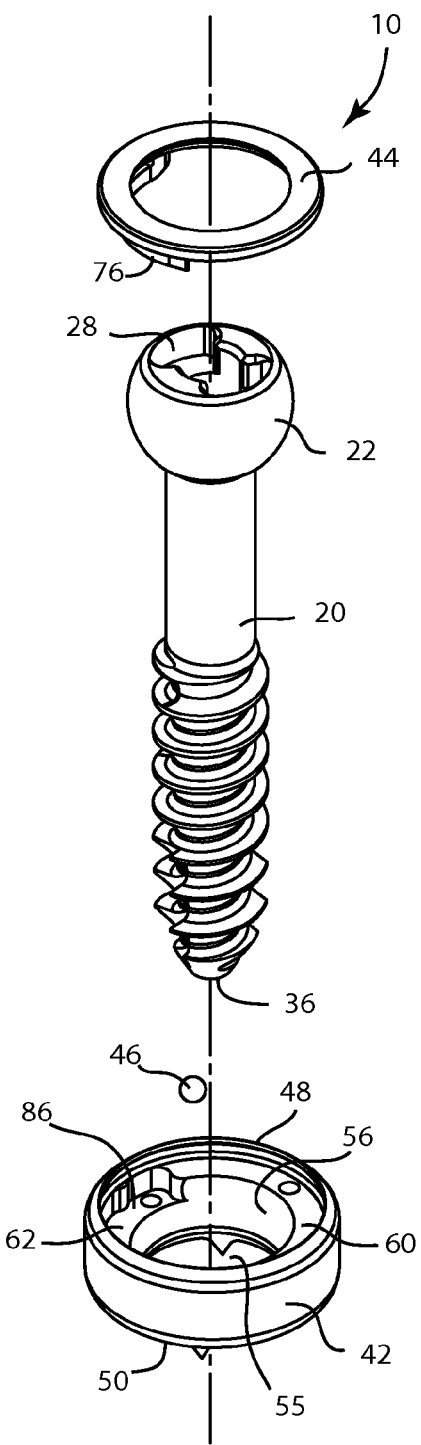
FIG. 4A illustrates a top perspective exploded view of the system of FIG. 1A.
Figure 4B:
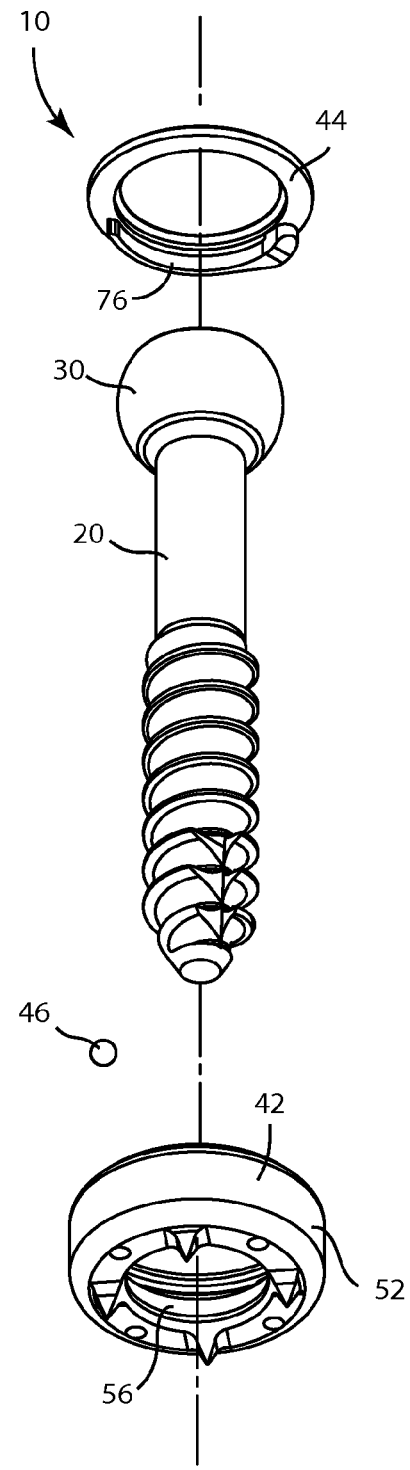
FIG. 4B illustrates a bottom perspective exploded view of the system of FIG. 1A.

Washer assembly 40 includes a washer 42 and cap 44. The washer assembly may further include a ball 46 (as best seen in FIGS. 4A and 4B) which is captured between the washer 42, the cap 44, and the head 22 when the washer assembly is operatively assembled with the screw 20 as in FIGS. 1A and 1B. The system 10 may be operatively assembled during manufacture and provided to the end users in the operatively assembled form, in sterile packaging.

Figure 2A:
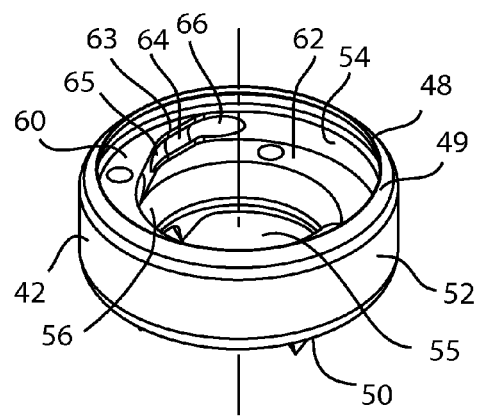
FIG. 2A illustrates a top perspective view of a washer of the washer assembly of FIG. 1A.
Figure 2B:
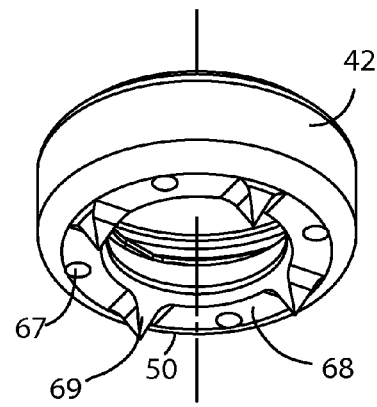
FIG. 2B illustrates a bottom perspective view of the washer of FIG. 2A.
Figure 2C:
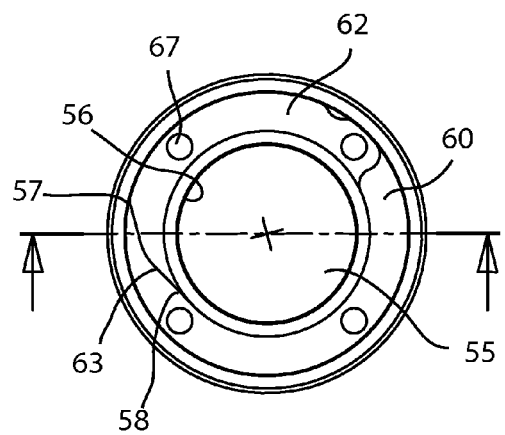
FIG. 2C illustrates a top view of the washer of FIG. 2A.
Figure 2D:
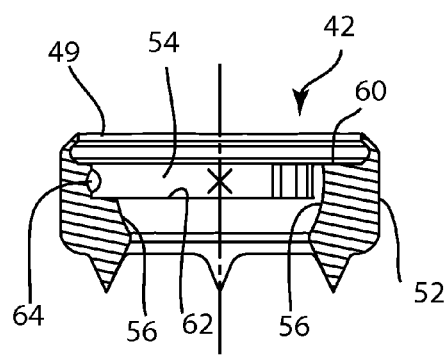
FIG. 2D illustrates a side cross-sectional view of the washer of FIG. 2A.
Figure 3A:
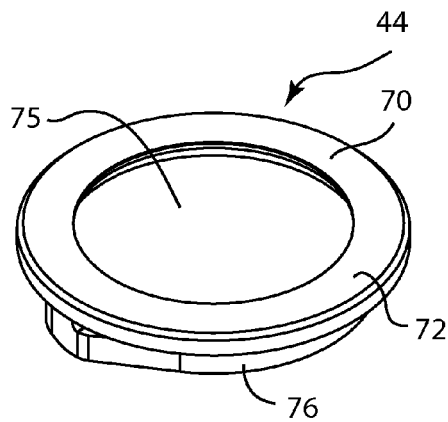
FIG. 3A illustrates a top perspective view of a cap of the washer assembly of FIG. 1A.
Figure 3B:
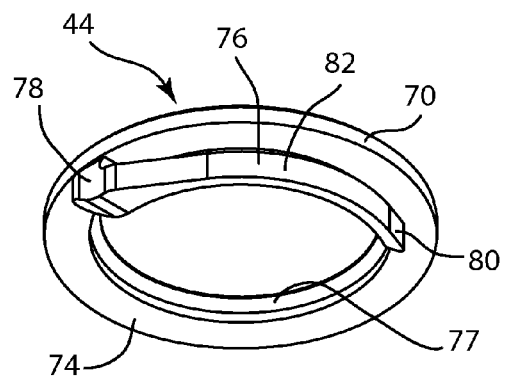
FIG. 3B illustrates a bottom perspective view of the cap of FIG. 3A.
Figure 3C:
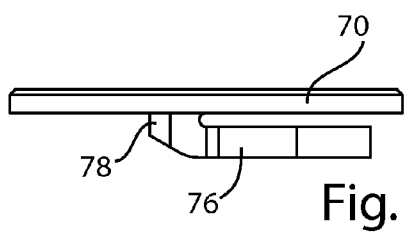
FIG. 3C illustrates a side view of the cap of FIG. 3A.
Figure 3D:
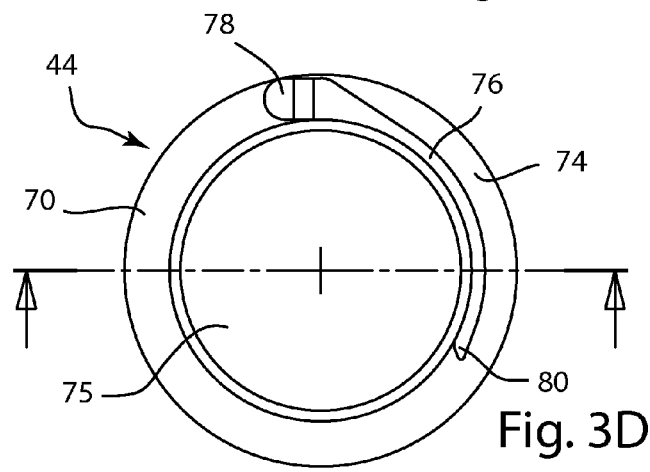
FIG. 3D illustrates a bottom view of the cap of FIG. 3A.
Figure 3E:
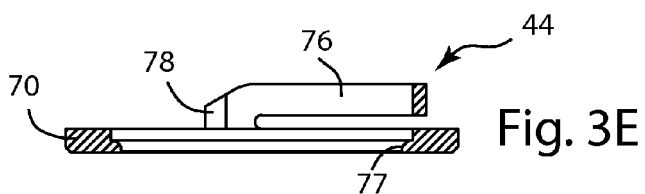
FIG. 3E illustrates a side cross-sectional view of the cap of FIG. 3A.

FIGS. 2A-2D show washer 42 in more detail. Washer 42 is annular, and has a first end 48 and a second end 50. First end 48 terminates with a relatively thin annular lip 49 which may project slightly toward the center of the washer 42. An outer peripheral wall 52 extends exteriorly between the first end 48 and the second end 50. An inner surface 54 extends interiorly between the first end 48 and the second end 50, forming a boundary to an aperture 55. An annular spherical recess 56 occupies a portion of the inner surface 54, and may form a socket to receive screw head 22. A portion of the annular spherical recess 56 is bounded toward the first end 48 by a first shelf 60, and the remainder is bounded toward the first end by a second shelf 62, which is recessed from, and may be described as lower than, the first shelf 60. Between the first shelf 60 and the second shelf 62, a portion of the inner surface 54 forms a ramp 63. The ramp 63 extends partially around the socket, or spherical recess 56, between a first end 57 which is outwardly displaced from the socket and a second end 58 which is tangential to the socket. An alcove 64 having a partial circular cross section is recessed into the inner surface 54; at least a portion of the alcove 64 overlaps the ramp 63, as seen in FIGS. 2A and 2D. Alcove 64 includes a first shallow portion 65 and a second deep portion 66, the depth of the alcove and the distance of the alcove from the spherical recess 56 increasing between the first and second portions. In this embodiment, alcove 64 has a cross section comprising an arc of a circle with a diameter which is complementary to the outer diameter of ball 46. The diameter of the circle may be slightly less than the outer diameter of ball 46, so that ball 46 is supported on the edges of alcove 64. Alcove 64 may be further described as a semicircular dished face, or a groove.

At least one bore 67 may extend longitudinally through the washer between the first end 48 and the second end 50, and may, for example, provide access for cleaning during or after manufacturing. The second end 50 of the washer 42 includes a bone engagement surface 68, at least a portion of which may be compressed against bone material when the screw system is implanted. At least one spike 69 protrudes from the second end 50. The spikes 69 may penetrate bone to provide additional fixation and/or rotation prevention. In other embodiments, pegs, nails, pins, keels or other bone-penetrating features may be included in place of or in addition to spikes 69, or no bone-penetrating features may be included. The bone engagement surface 68 may be roughened or porous to promote bone ongrowth or ingrowth; bone growth or other therapeutic agents may also be provided on the bone engagement surface 68.

Referring to FIGS. 3A-3E, the cap 44 includes a ring 70, the ring having a first side 72 and a second side 74 with an aperture 75 extending through the ring between the first and second sides 72, 74. A beam 76, which may be a cantilever beam, projects from the second side 74. A fixed end 78 of the beam is fixed to the ring, and a free end 80 is adjacent, but unconnected to, the ring 70. A beam body 82 extends between the fixed end 78 and the free end 80, is curved to follow the curvature of the ring 70, and may be parallel to the ring 70. The beam 76 may have the same radius of curvature as the ring 70, so that it extends along and overlaps a portion of the ring 70. The aperture 75 may include a lip 77 which has a diameter smaller than the equatorial diameter of the screw head 22.

Figure 5B:
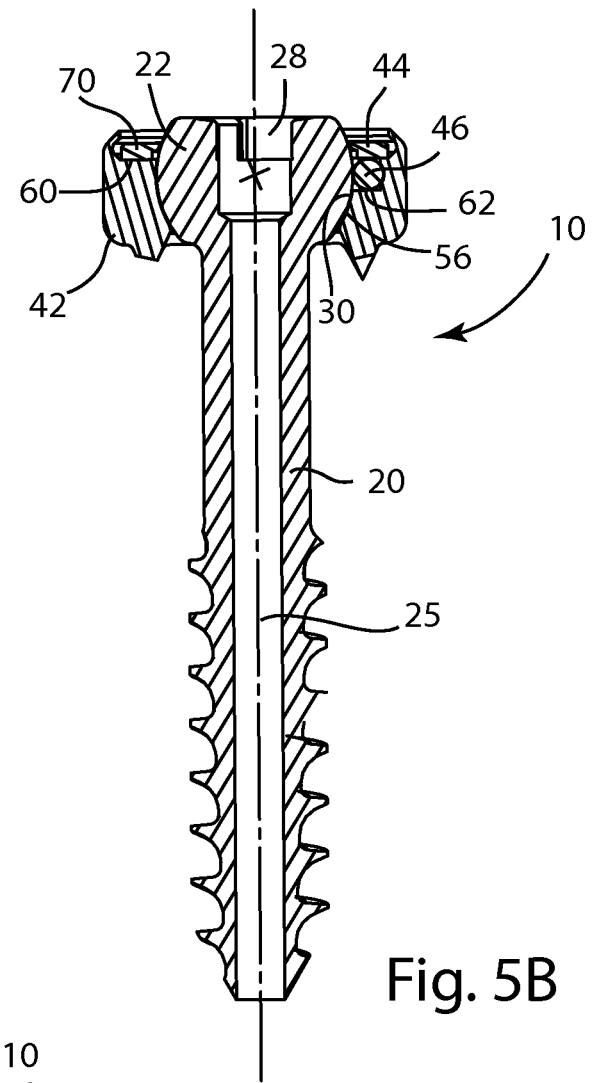
FIG. 5B illustrates a longitudinal cross-sectional view of the system of FIG. 5A.
Figure 5A:
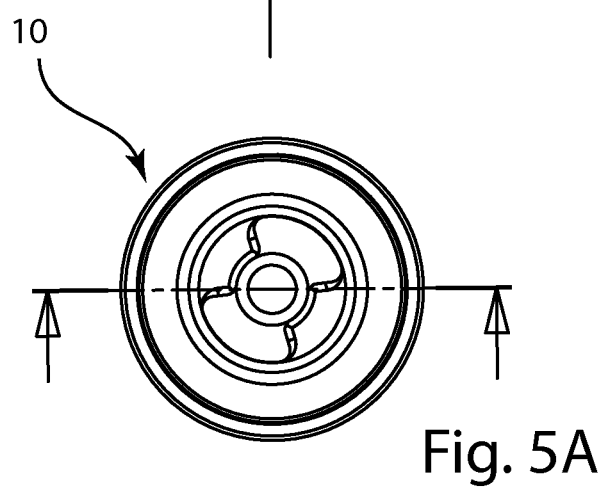
FIG. 5A illustrates a top view of the system of FIG. 1A.
Figure 6:
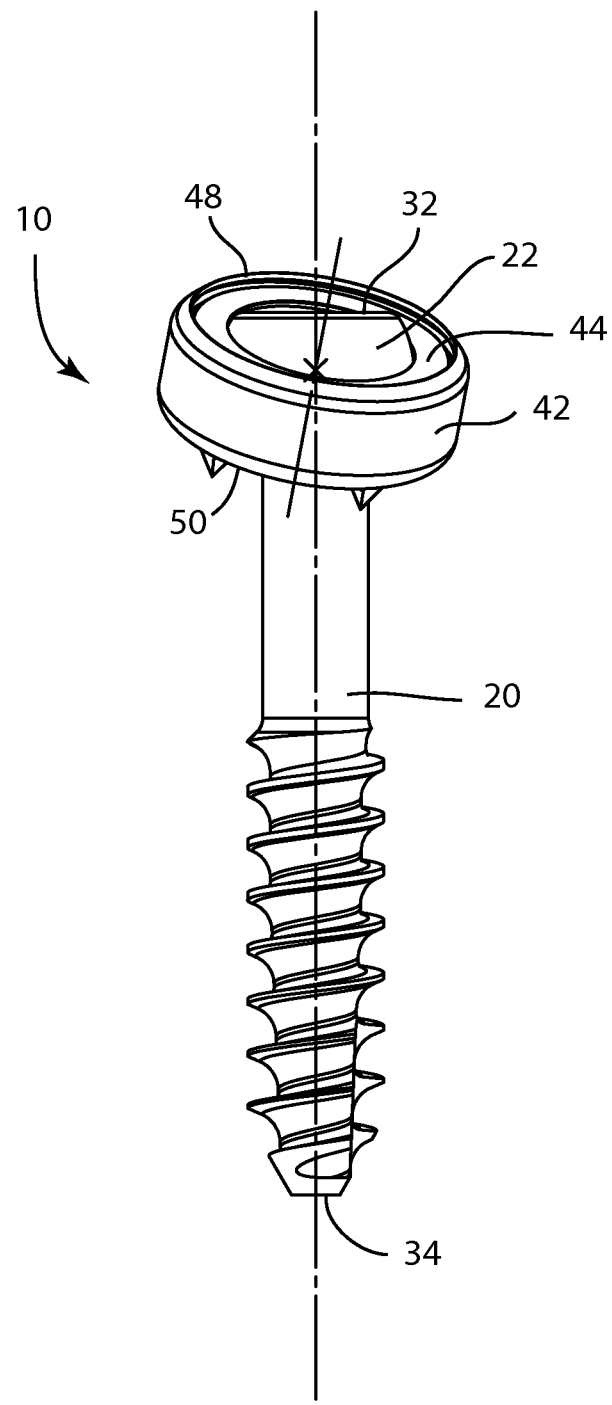
FIG. 6 illustrates a top perspective view of the system of FIG. 1A, showing the washer assembly polyaxially pivoted relative to the screw.
Figure 7A:
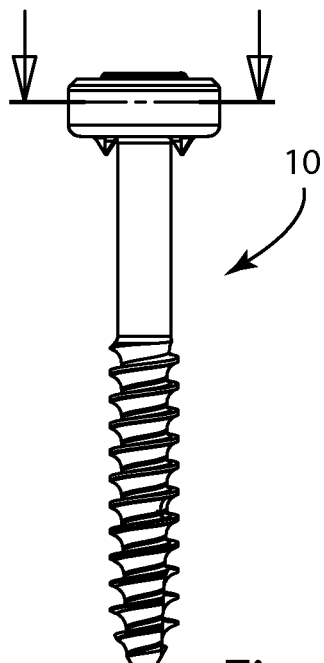
FIG. 7A illustrates a side view of the system of FIG. 1A.
Figure 7B:
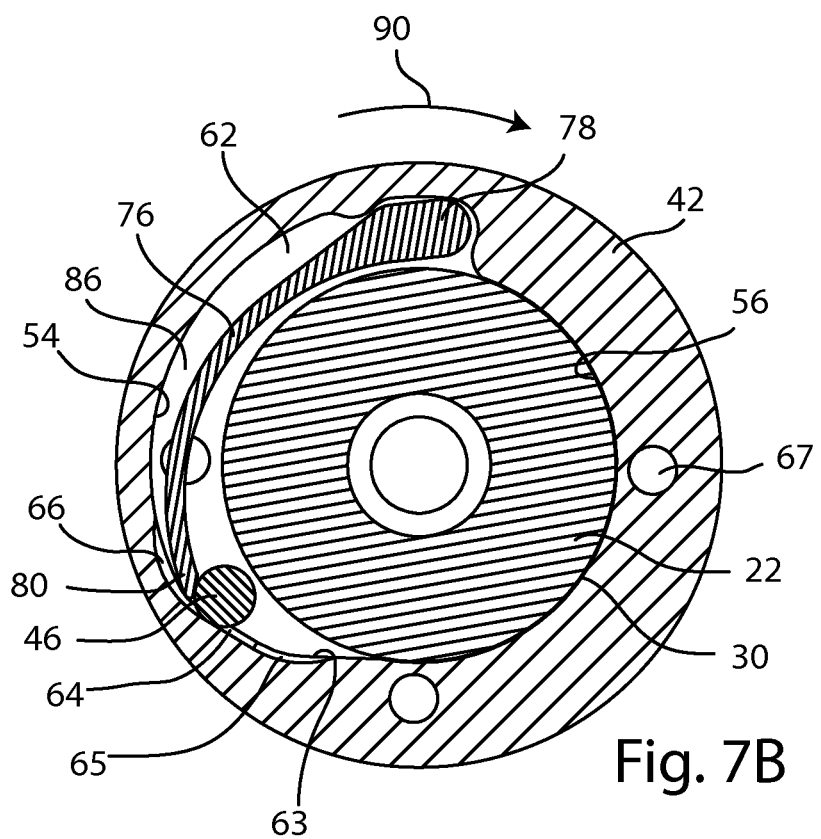
FIG. 7B illustrates a top cross-sectional view of the system of FIG. 7A with the system in an unlocked configuration in which the screw can rotate freely in a first direction relative to the washer assembly.
Figure 8A:
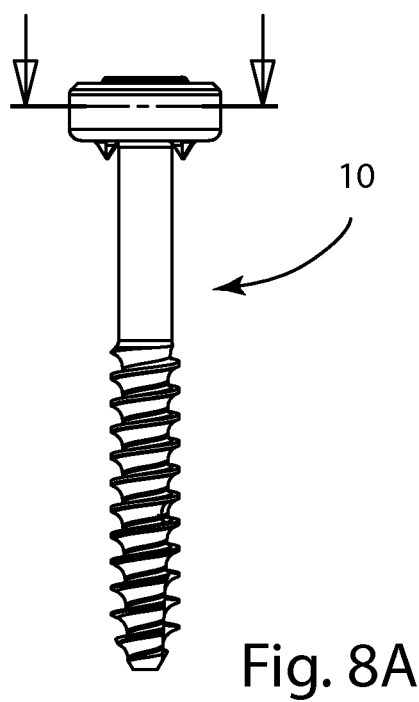
FIG. 8A illustrates a side view of the system of FIG. 1A.
Figure 8B:
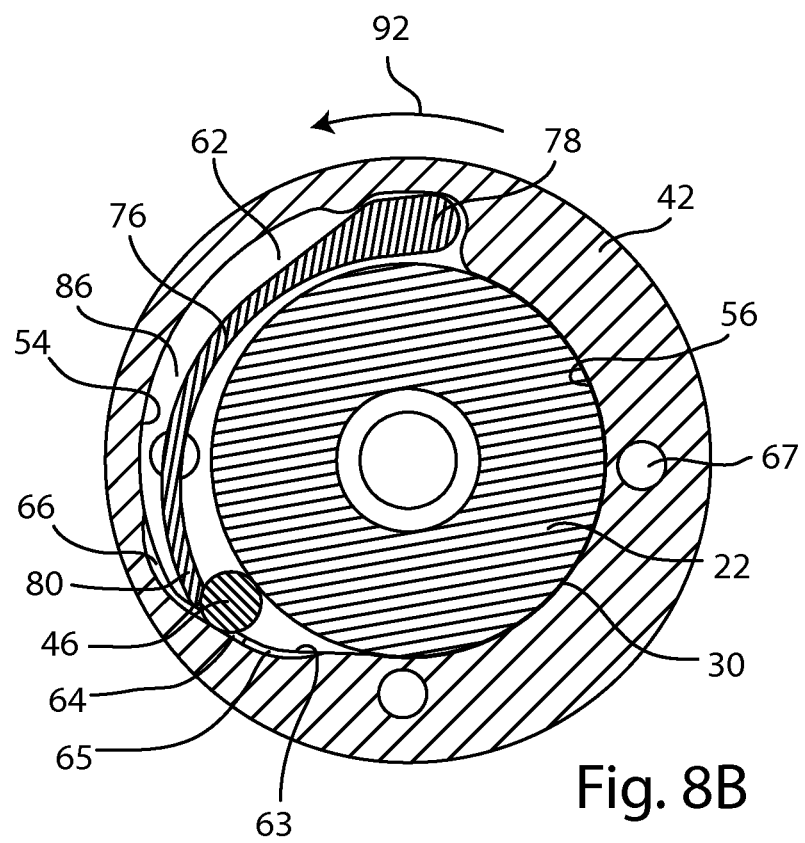
FIG. 8B illustrates a top cross-sectional view of the system of FIG. 8A with the system in a locked configuration in which the screw and washer assembly are frictionally locked together so that the screw is unable to rotate freely in a second direction relative to the washer assembly.

FIGS. 4A-4B depict screw system 10 in exploded views, and FIG. 5B is a cross-sectional view of the system in an operatively assembled configuration. When system 10 is assembled, screw 20 is received through washer 42, with tip 36 oriented in the same general direction as second end 50, and head 22 toward first end 48. Screw head 22 is retained by washer 42, with spherical bearing surface 30 bearing against annular spherical recess 56. Head 22 and washer 42 may thus form a ball and socket joint, with head 22 polyaxially pivotable relative to washer 42, as seen best in FIG. 6. Ball 46 is positioned inside washer 42 on second shelf 62, between head 22 and alcove 46. Cap 44 is positioned on washer 42, with a portion of ring 70 resting on first shelf 60. As best seen in FIGS. 7B and 8B, beam 76 extends from the second side 74 of the cap and is received in a gap 86 formed between head 22, second shelf 42, and inner surface 54 of washer 42. Free end 80 of beam 76 is adjacent alcove 64 of the washer, and ball 46 is between free end 80 and head 22. The free end 80 continuously spring biases the ball 46 toward the second end of the ramp 63. In other embodiments, ball 46 may be biased toward the second end of the ramp 63 by another kind of known spring, such as a spring clip, retaining ring, compression spring, extension spring, leaf spring, or torsion spring. In additional embodiments, ball 46 may be biased toward the second end of the ramp 63 by other known biasing means, such as magnetic bias, gravitational bias, or shape memory bias. Cap 44 is secured to washer 42 through a press-fit connection; as cap is pressed onto washer 42 in the described position, lip 49 of the washer may be deformed. In other embodiments, cap 44 may be secured to washer 42 by laser welding, a snap fit, a taper fit, a friction fit, threads, or any other known suitable connection means. It is appreciated that head 22 is polyaxially pivotable relative to washer 42 both before and after cap 44 is attached to washer 42.

Referring to FIGS. 7B and 8B, when screw system 10 is operatively assembled, screw 20 can rotate freely relative to washer assembly 40 in a first direction, but becomes rigidly locked to washer assembly 40 when rotated in a second direction. As shown in FIG. 7B, head 22 may be freely rotated in a first direction 90, which may be clockwise. As head 22 rotates, ball 46 is urged along alcove 64 in ramp 63, from shallow portion 65 toward deep portion 66. As ball 46 encounters free end 80 of beam 76, the beam is deflected toward deep portion 66, and the spring bias of the beam is temporarily overcome, allowing free rotation of the head 22. Although in FIG. 7B a small gap is shown between ball 46 and head 22, it is appreciated that ball 46 and head 22 may be in slight contact, yet head 22 is still able to freely rotate relative to washer 42.

As shown in FIG. 8B, rotation of head 22 in a second direction 92, which may be counterclockwise and opposite the first direction, causes a frictional lock to form between head 22 and washer assembly 40. As head 22 is rotated in the second direction 92, ball 46 is urged along alcove 64 in ramp 63 toward shallow end 65. Ball 46 is further urged toward shallow end 65 by the spring bias of beam 76. Ball 46 becomes jammed or wedged between alcove 64 and head 22, and may be deformed against head 22 as a result of the wedging action. In the present embodiment, ball 46 becomes wedged between two points of contact along the edges of alcove 64 and a single point of contact with head 22; the single point of contact may transform into a contact patch or area due to deformation of the ball 46 against the head 22. Further rotation of head 22 in the second direction is prevented; however washer 42 may still be polyaxially pivotable relative to head 22.

In one method of use, screw system 10 may be implanted across a facet joint to provide joint fixation, preventing articulation of the joint. A guidewire may be inserted across the joint, and a cannula inserted over the guidewire to the proximal facet. A cannula insertion instrument providing tissue dilation and cannula insertion, such as that disclosed in U.S. Provisional Patent Application No. 61/374,862, incorporated by reference into this disclosure, may be used to insert the cannula. The cannula may be temporarily docked to the proximal facet. The operatively assembled screw system 10 may be inserted through the cannula to the facet joint, with the screw first end 34 leading. A driver is used to rotate screw 20 in the first direction 90, driving screw 20 through the facets and across the joint. As screw 20 is driven, washer 42 comes in contact with the proximal facet, with at least a portion of bone engagement surface 68 in contact with the bony material of the facet. The polyaxial adjustability of the washer assembly relative to the screw allows the washer to sit at an angled position relative to the screw, which may be dictated by the surface topography of the facet and/or the surrounding environment. As screw 20 is driven further, spikes 69 may penetrate the surface of the facet, providing enhanced fixation and anti-rotation. When desired fixation of the joint and compression of the washer against the facet is achieved, rotation of screw 20 is ceased. Unintentional back-out and/or unintentional loosening of screw system 10 is prevented, as any rotation of screw 20 in second direction 92 results in locking together of screw 20 and washer assembly 40. Since washer assembly 40 is stabilized against the facet by spikes 69, screw 20 is effectively prevented from backing out or loosening.

Screw system 10 may be used in other applications in which two bone segments are fixed or compressed together to provide fixation or arthrodesis of a joint. The system may also be used in any orthopedic application in which anti-backout capabilities are desired, for example, to attach a prosthesis or implant to a bone. Non-limiting examples include attachment of articulating facet joint prostheses to vertebrae, attachment of intervertebral disk replacement prostheses, attachment of spinal rods, attachment of bone plates, and attachment of other joint prostheses, including knee, hip, shoulder, wrist, and/or ankle prostheses. Screw system 10 may also provide an anchor for anchoring of sutures, or natural or artificial tissues such as muscle, tendon, or ligament. One of skill in the art may appreciate that washer assembly 40, for example, may be modified by replacing washer 42 with an alternate component, which may include some or all of the features described above for washer 42.

Figure 9:
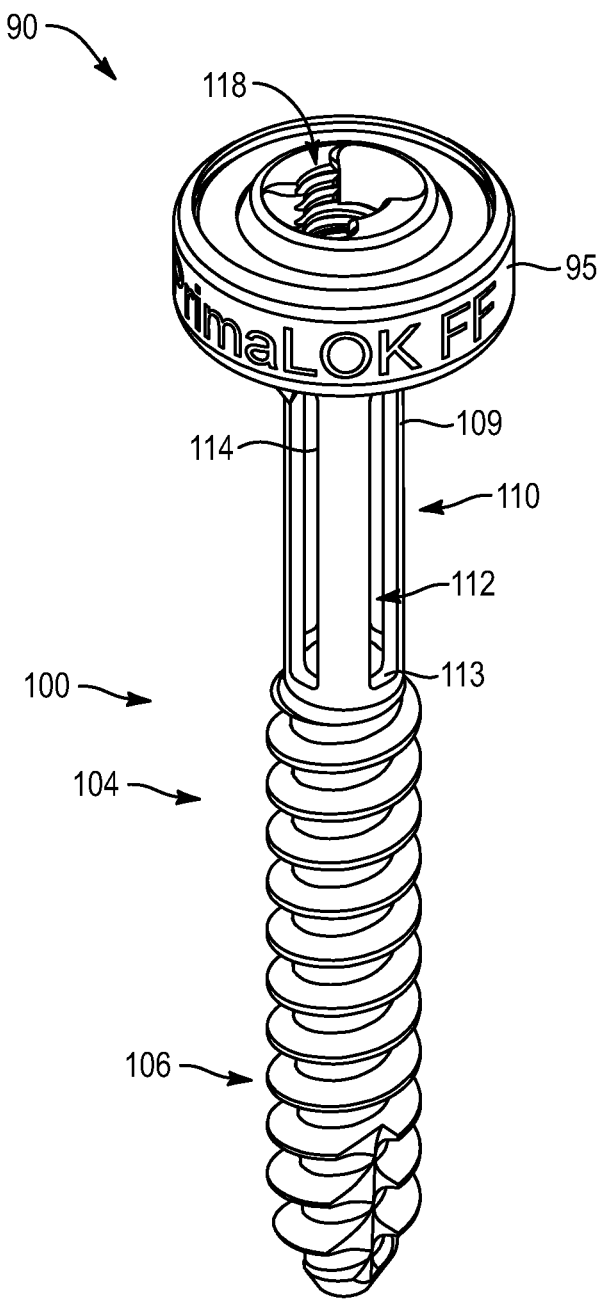
FIG. 9 illustrates a perspective view of a system including a screw and a washer.
Figure 10:
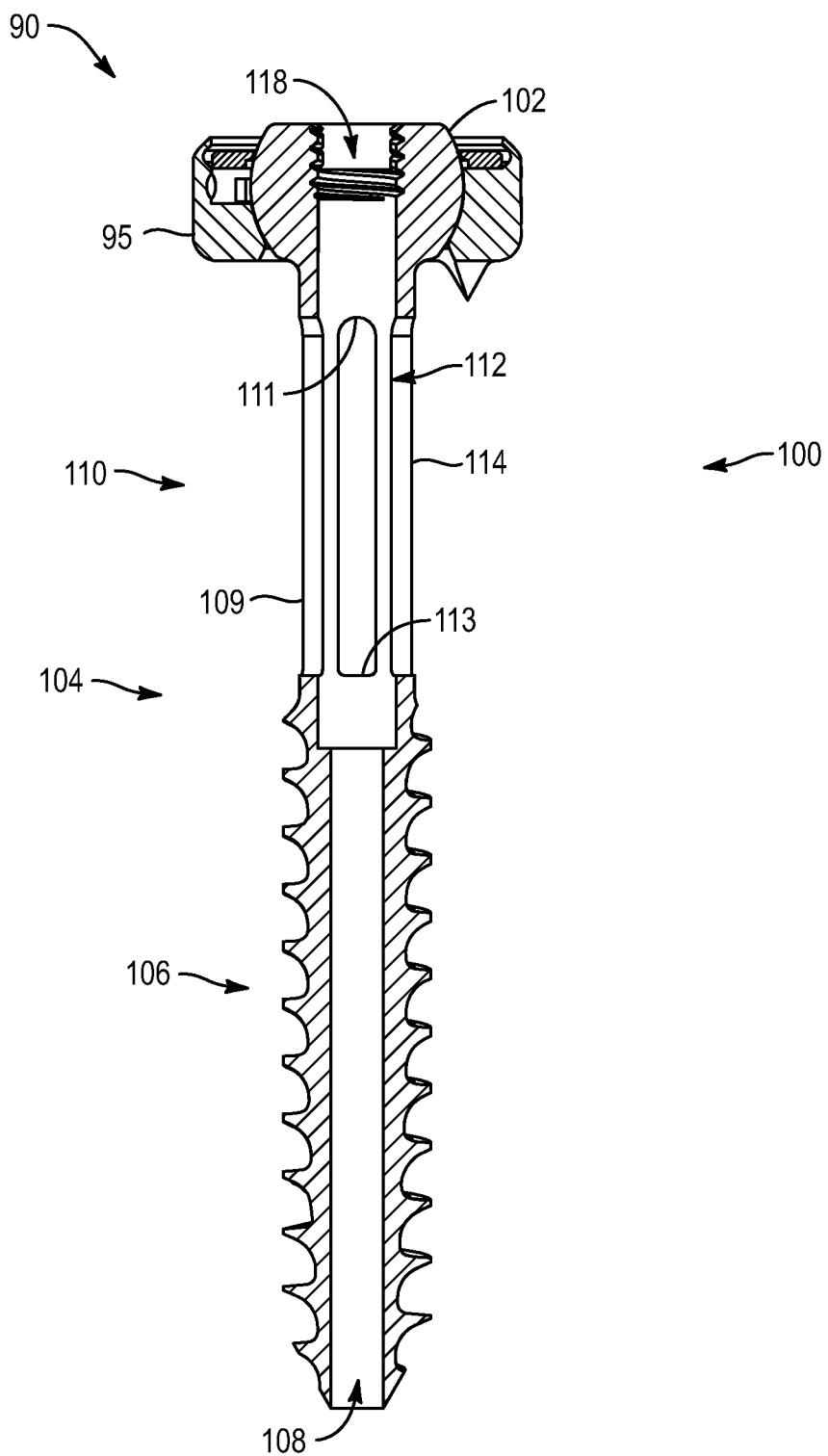
FIG. 10 illustrates a cross section of the system of FIG. 9.

FIGS. 9-10 illustrate an example of a polyaxial facet fusion screw system 90 including a screw 100 and a washer 95.

Screw 100 may be based on and share at least some characteristics with previously described screw 20. Referring to FIG. 9, the screw 100 includes a spherical head 102 and a shaft 104 extending from the head, wherein shaft 104 includes a distal threaded portion 106 and an empty proximal cylindrical cavity 110. A frame 109 surrounding the proximal cylindrical cavity 110 may be pierced with at least one aperture 112. Four apertures 112 are shown in the illustrated example of screw 100. The aperture 112 may extend the full length of the cylindrical cavity 110, or extend only a portion of the length of the cavity. The aperture has a proximal surface 111 and a distal base surface 113. Flanking the aperture 112 are columns 114 that support the cylindrical cavity 110 and the head 102 of the screw 100. A cannulation 108 may extend along the shaft 104 so that the screw 100 may be driven over a guide wire. Cannulation 108 may intersect the proximal cylindrical cavity 110 in a middle portion of shaft 104. An opening 118 may extend through the top of the screw 100 to provide access to the cylindrical cavity 110, however, access to the cylindrical cavity 110 may be provided from other directions as well.

Washer 95 may share some or all of the characteristics set forth for the previously described washer 42 or washer assembly 40.

Figure 11:
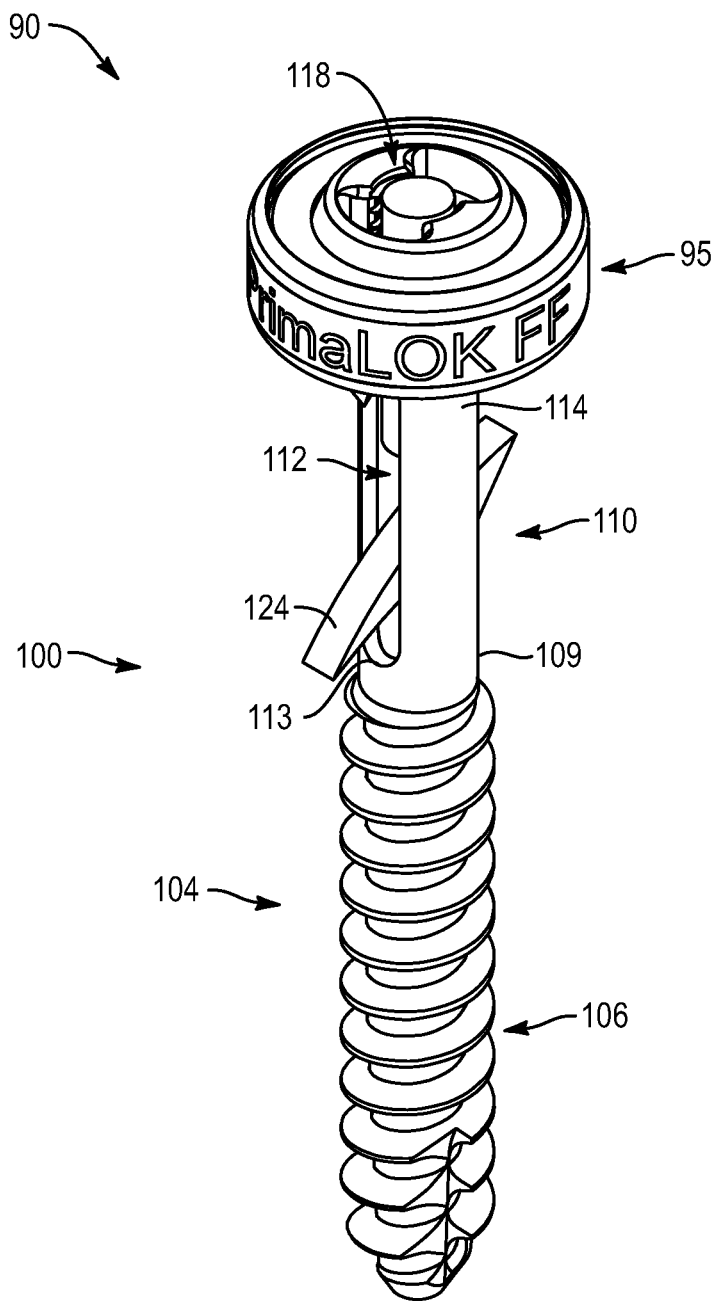
FIG. 11 illustrates a perspective view of the system of FIG. 9 with an auxiliary fixation feature in a deployed configuration.
Figure 12:
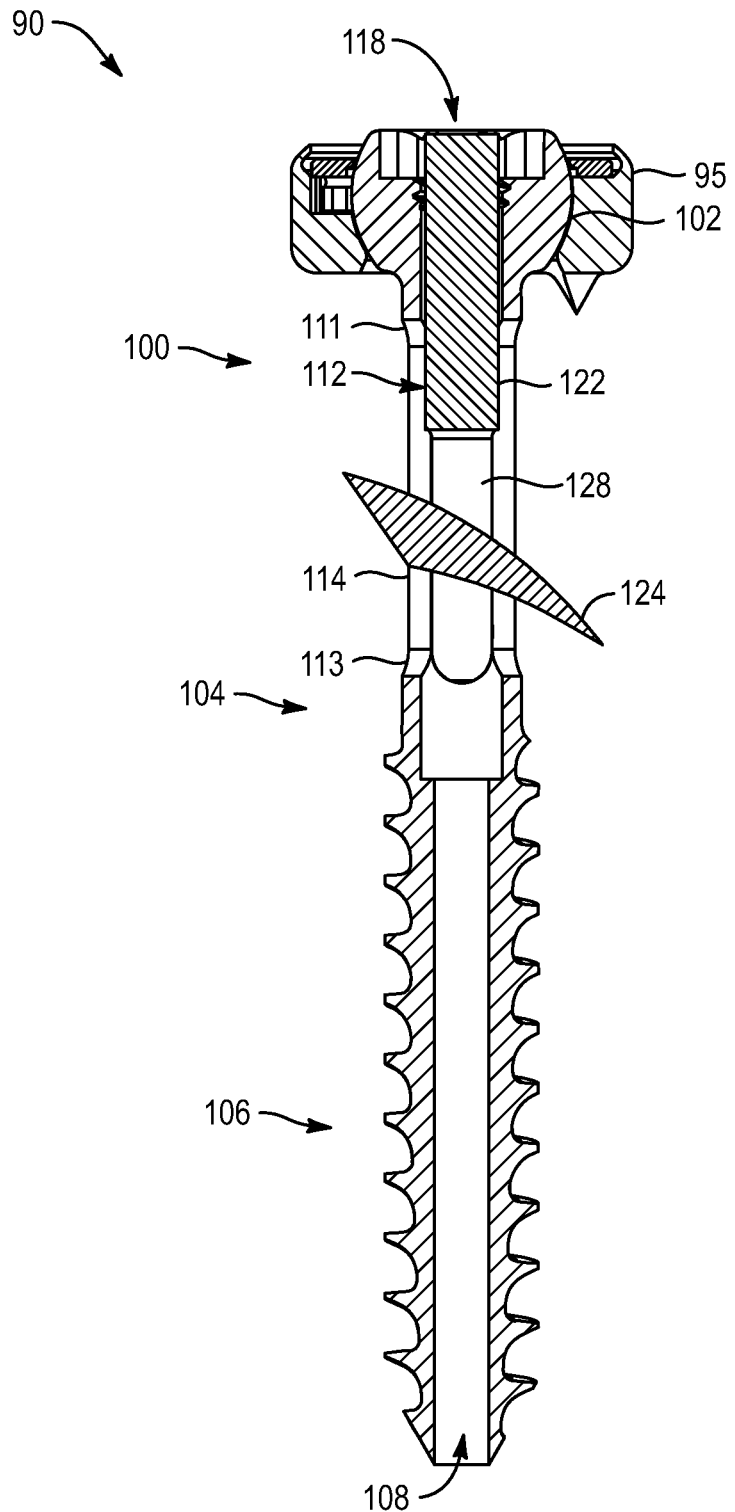
FIG. 12 illustrates a cross section of the screw system and auxiliary fixation feature of FIG. 11.
Figure 13:
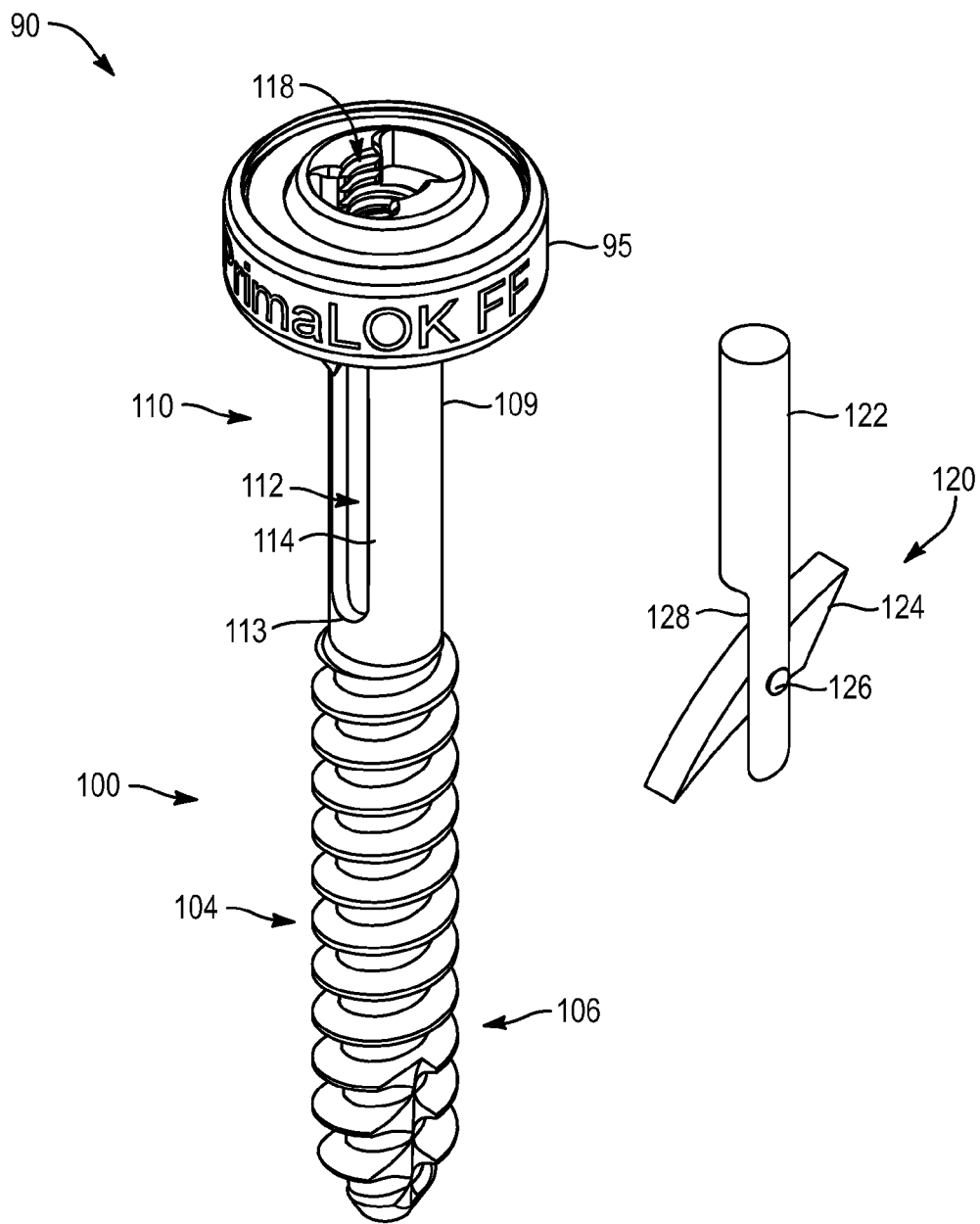
FIG. 13 illustrates an exploded view of the screw system and auxiliary fixation feature of FIG. 11.

FIGS. 11-13 illustrate an example of the screw 100 and washer 95 combined with an auxiliary fixation feature 120.

The auxiliary fixation feature 120 may be formed separately from screw 100 and washer 95. With reference to FIG. 13, the auxiliary fixation feature 120 includes a rod 122 and a fin 124. The rod 122 may be solid or cannulated. The rod 124 may be of a complementary shape to the interior of the cylindrical cavity 110. The rod 122 may include a recessed portion 128, which may be located in a distal portion of the rod. The fin 124 may be formed separately from the rod 122. The fin 124 shown in FIGS. 11-13 is generally triangular, however, other polygonal or curved shapes may be contemplated. The fin 124 may be hinged to at least one side of the rod 122 with a pivot 126. For example, the fin 124 may be hinged to the rod 122 in the recessed portion 128. The fin 124 may also be bilaterally attached to the rod 122, for example in a central recess, clevis, or slot in the rod. The pivot 126 may be a pin or other type of fastener.

The auxiliary fixation feature 120 may be operatively assembled with screw 100 by inserting the auxiliary fixation feature 120 into the cylindrical cavity 110, as seen best in FIGS. 11 and 12. For example, the fin 124 may be rotated into alignment with rod 122 so that auxiliary fixation feature 120 may slide unimpeded through opening 118 and into cylindrical cavity 110. This arrangement of the auxiliary fixation feature 120 may be described as an insertion configuration. In one example, the auxiliary fixation feature 120 may be inserted into the screw 100 so that fin 124 rests against a column 114 so that the fin cannot inadvertently protrude from the shaft 104 of the screw 100. In another example, the auxiliary fixation feature 120 may be inserted into the screw 100 so that fin 124 is axially displaced relative to the aperture 112 to prevent inadvertent protrusion. In yet another example, a tip end of the fin 124 may protrude into the aperture 112. The fin 124 may remain in the insertion position while screw system 90 is inserted, thus providing no resistance to screw insertion.

Once screw system 90 is in place, auxiliary fixation feature 120 can be repositioned such that the fin 124 becomes aligned with the aperture 112 in the frame 109 of the cylindrical cavity 110. The fin 124 can then extend through the aperture 112 and transition via manual or automatic repositioning to a deployed configuration, which may provide resistance to screw removal. For example, the auxiliary fixation feature 120 may be transformed between the insertion and deployed configurations by rotating and/or axially translating the auxiliary fixation feature relative to the screw 100 with a tool. A tip end of the fin 124 may interact with, or slide across, the proximal and/or distal surfaces 111, 113 to urge the fin 124 towards the deployed configuration.

FIGS. 11 and 12 depict auxiliary fixation feature 120 in a deployed configuration, in which at least a portion of auxiliary fixation feature 120 protrudes beyond the shaft 104. In the example shown, the protruding portion of auxiliary fixation feature 120 is the fin 124, however the protruding portion may also be described as, or formed as, a barb, keel, prong, spike, or blade. FIG. 12 is a cross sectional view of screw 100 operatively assembled with auxiliary fixation feature 120 in the deployed position, in which the fin 124 is laterally oriented across the width of the proximal cylindrical cavity 110 and extends outward beyond the shaft 104 through the apertures 112 located in the frame 109 of the cavity.

In one method of use, auxiliary fixation feature 120 may be biased to extend outward from rod 122. In other words, the fin 124 may be biased to extend transversely across the rod 122. Auxiliary fixation feature 120 may be biased with a spring or magnet. During assembly, fin 124 is in the insertion position, in which the bias may be temporarily overcome so that fin 124 is oriented parallel or nearly parallel to rod 122. In this position, fin 124 is substantially contained within the shaft 104 during assembly. Auxiliary fixation feature 120 may also be biased through the interaction of features on the fin 124, rod 122, and/or screw 100. For example, in the insertion configuration, a tip end of the fin 124 may protrude into the aperture 112 so that further advancement of the auxiliary fixation feature 120 urges the fin to rotate into the deployed configuration. If the auxiliary fixation feature is biased, the fin 124 may automatically transition to the deployed configuration as soon as the fin 124 is aligned with the aperture 112.

Figure 14:
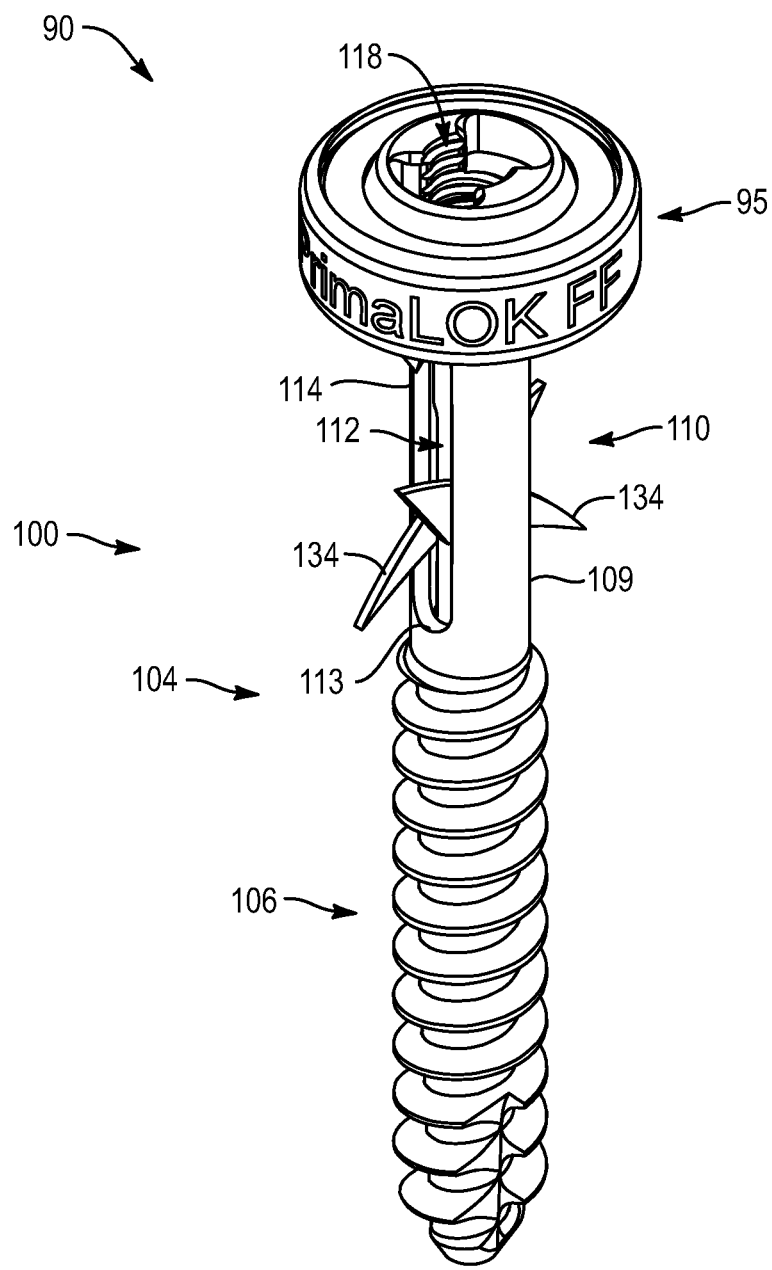
FIG. 14 illustrates a perspective view of the system of FIG. 9 with another auxiliary fixation feature in a deployed configuration.
Figure 15:
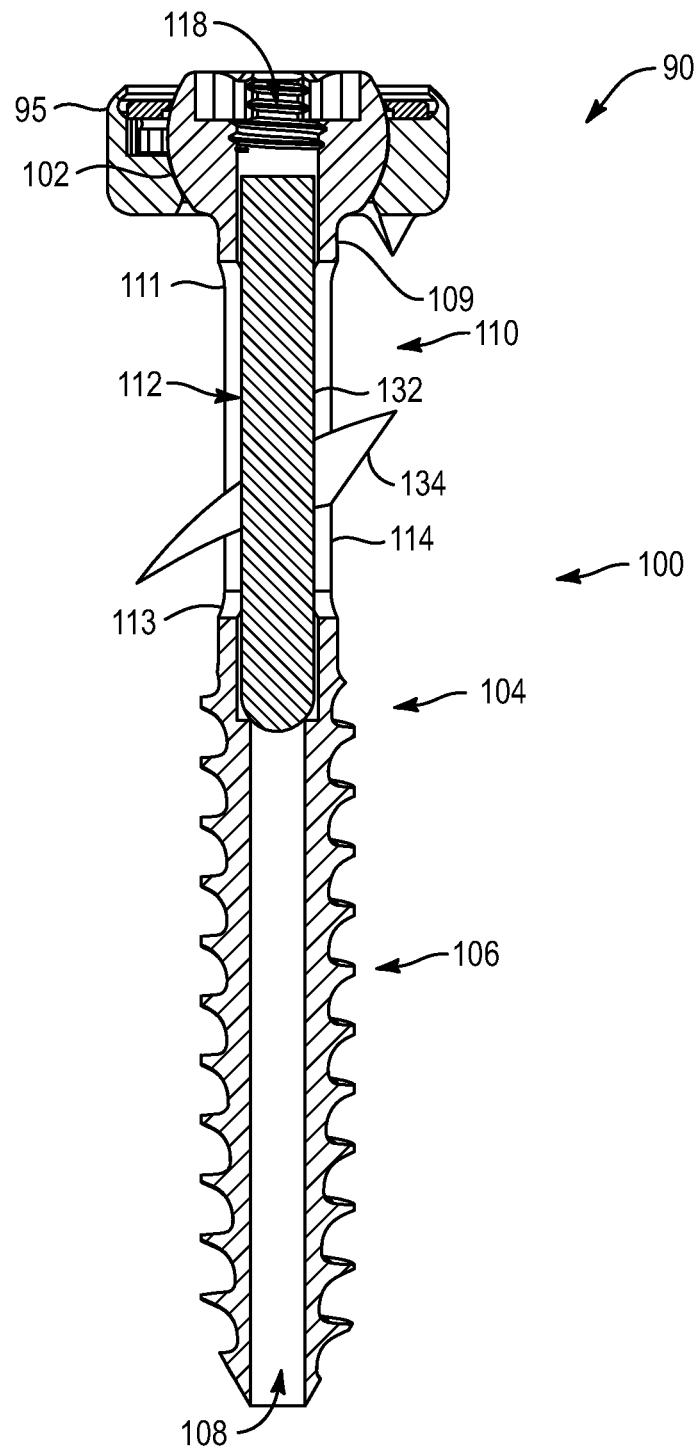
FIG. 15 illustrates a cross section of the screw system and auxiliary fixation feature of FIG. 14.
Figure 16:
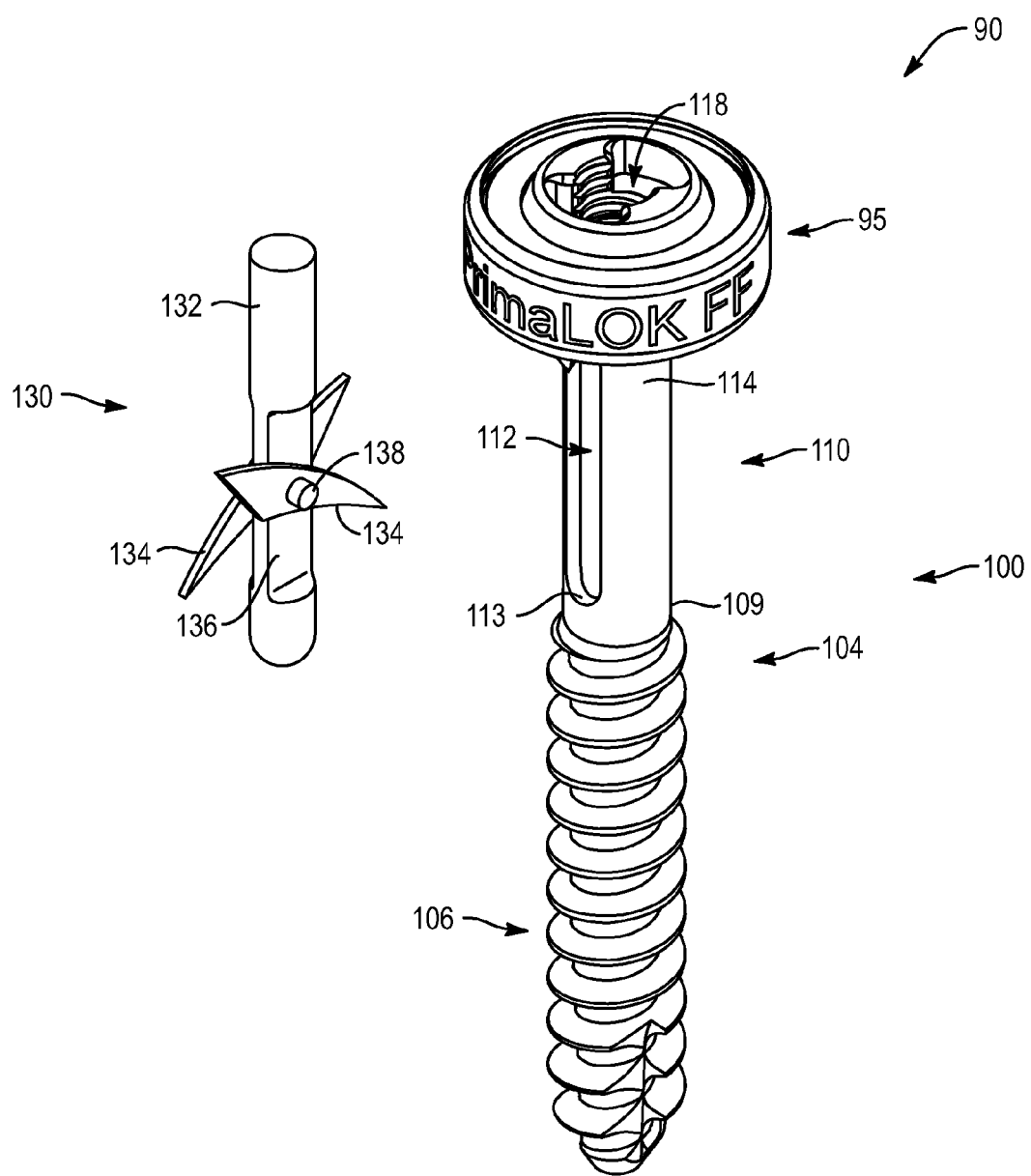
FIG. 16 illustrates an exploded view of the screw system and auxiliary fixation feature of FIG. 14.

FIGS. 14-16 illustrate an example of screw system 90 with another auxiliary fixation feature 130.

The auxiliary fixation feature 130 is formed separately from screw 100. With reference to FIG. 16, the auxiliary fixation feature 130 includes a rod 132 and two fins 134. The rod 132 may be solid or cannulated. The rod 132 may be of a complementary shape to the interior of cylindrical cavity 110. The rod 132 may include bilateral recessed portions 138 in which fins 134 can be attached. The recessed portions 138 may be located in a distal portion of the rod 132. The fins 134 may be attached to the rod 132 via a pivot 138, which may be a pin or other fastener.

The auxiliary fixation feature 130 can be operatively assembled with screw 100 by inserting the auxiliary fixation feature 130 into the cylindrical cavity 110, as seen best in FIGS. 14 and 15. For example, the fins 134 may be rotated into alignment with the rod 132 so that auxiliary fixation feature 130 may slide unimpeded through opening 118 into cavity 110. This arrangement of the auxiliary fixation feature 130 may be described as an insertion configuration. In this position, the fins 134 are substantially contained within the shaft 104, thus providing little or no resistance to assembly of the screw system 90 and auxiliary fixation feature 130 or to screw insertion. The fins 134 may be axially or rotationally mis-aligned with, or offset from, the aperture(s) 112 to prevent unintentional protrusion of the fins from the screw 100. The auxiliary fixation feature 130 may remain in the insertion position while screw system 90 is inserted, thus providing no resistance to screw insertion.

Once screw system 90 is in place, auxiliary fixation feature 130 may be repositioned such that the fins 134 align with the apertures 112. The fins 134 can then extend through the apertures 112 beyond the shaft 104 via manual or automatic repositioning.

FIGS. 14 and 15 depict double-finned auxiliary fixation feature 130 in a deployed configuration. In this example, the two fins 134 may protrude beyond the shaft 104 opposite one another.

In one method of use, the fins 134 may be biased to extend outward from rod 132. In the insertion position, the bias may be temporarily overcome so that fins 134 lay parallel or near parallel to the rod 132. If auxiliary fixation feature 130 is biased, it may automatically deploy as soon as the fins 134 are aligned with the aperture(s) 112.

Figure 17:
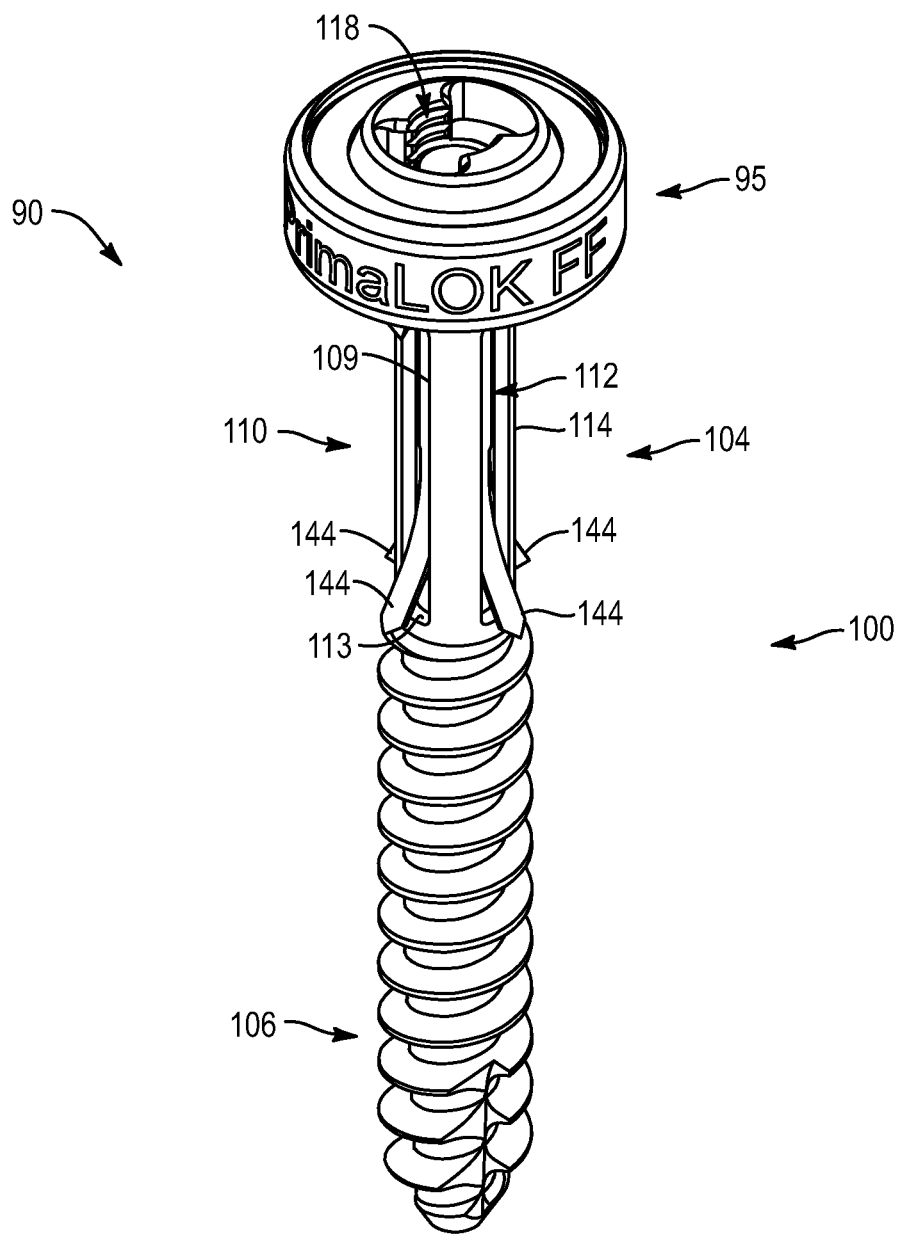
FIG. 17 illustrates the screw system of FIG. 9 with yet another auxiliary fixation feature in a deployed position.
Figure 18:
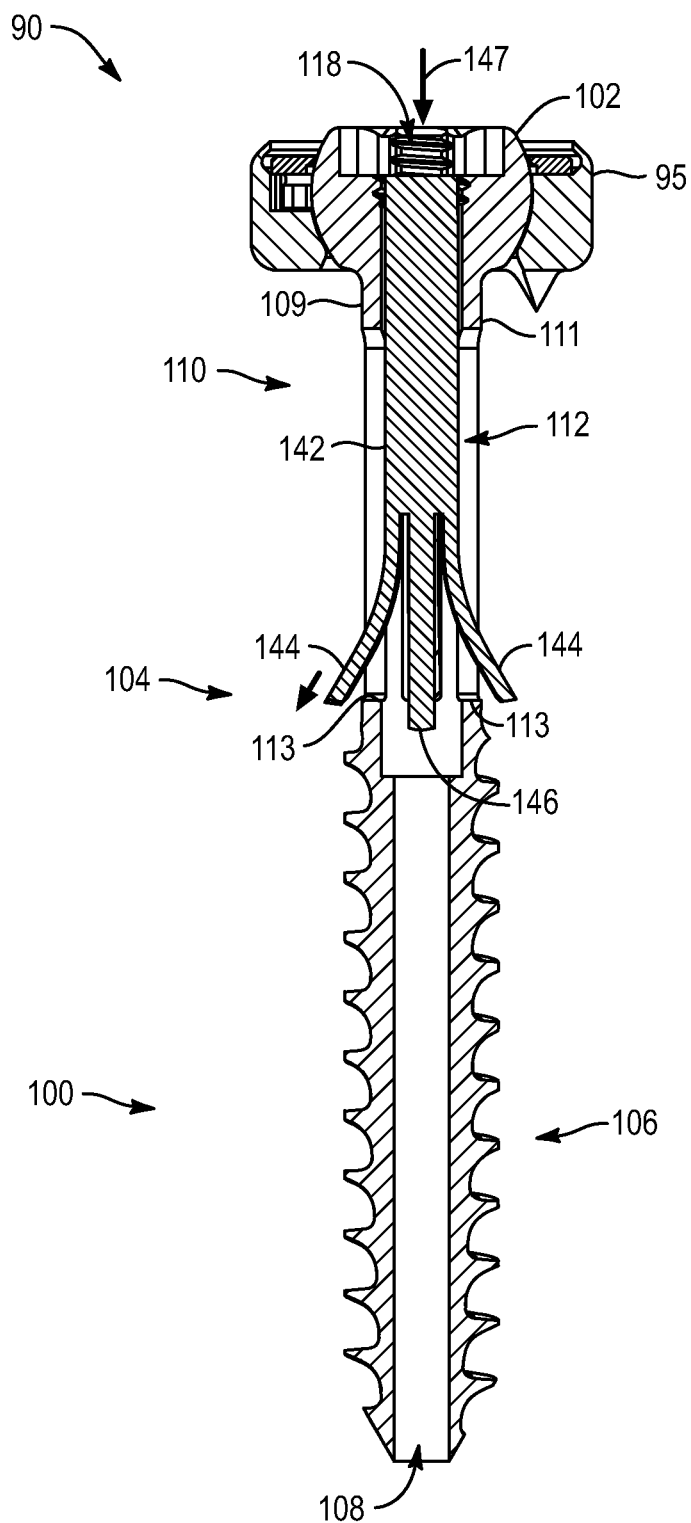
FIG. 18 illustrates a cross section of the screw system and auxiliary fixation feature of FIG. 17.
Figure 19:
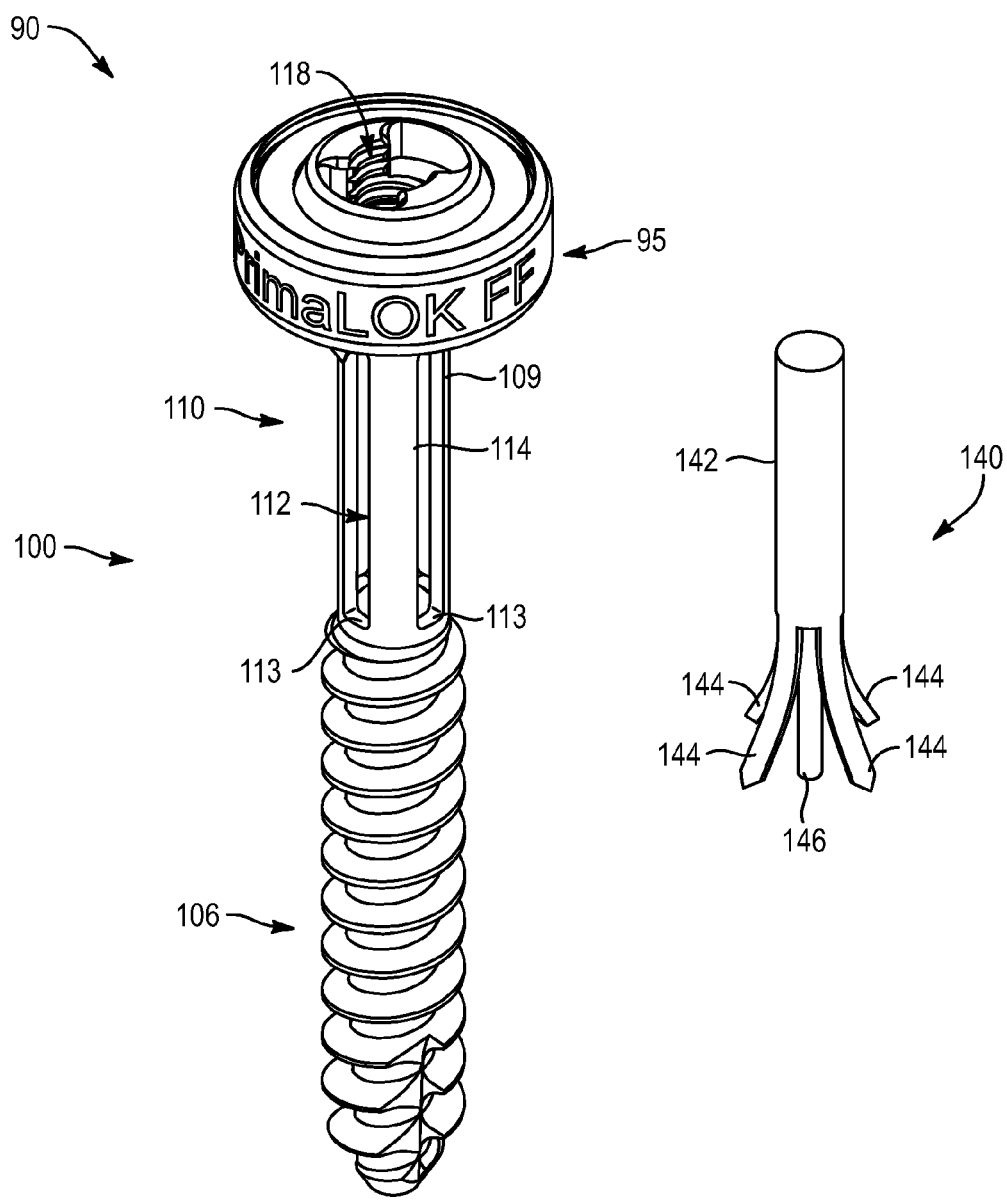
FIG. 19 illustrates an exploded view of the screw system and auxiliary fixation feature of FIG. 17.

FIGS. 17-19 illustrate an example of screw 100 and washer 95 with yet another auxiliary fixation feature 140.

Auxiliary fixation feature 140 is formed separately from screw 100 and can be operatively assembled with screw 100 as best seen in FIGS. 17 and 18. Auxiliary fixation feature 140 includes a rod 142, a pin 146, and at least one prong 144. The rod 142 may be a solid cylinder, or have a hollow center. The pin 146 may extend distally from the rod 142. The prong 144 may extend from the distal portion of rod 142 beside the pin 146. For example, FIG. 19 shows four prongs 144 arranged around centrally located pin 146. The prong 144 may have a neutral position parallel to rod 142, or near parallel with a slight bias outward. The pin 146 and prong 144 may be integral to rod 142.

The auxiliary fixation feature 140 may be operatively assembled with screw 100 through opening 118 into cavity 110. The prong(s) 144, if outwardly biased, may be compressed together in order to fit into opening 118 and cavity 110. This arrangement of auxiliary fixation feature 140 may be described as an insertion configuration, similar to those described previously. The prong(s) 144 may be intentionally misaligned with the aperture(s) 118 to prevent unintentional protrusion. The auxiliary fixation feature 140 may remain in the insertion position while screw system 90 is inserted, thus providing no resistance to screw insertion.

Once screw system 90 is in place, an axial distal force 147 may be placed on rod 142, causing pin 146 to advance distal to the cylindrical cavity 110 and enter the cannulation 108, and the prong 144 to contact the base surface 113 of aperture 112. The base 113 of aperture 112 may be wedged to provide additional guidance to prong 144, so that as distal force 147 is applied to rod 142, prong 144 may bend outward 149 from aperture 112 into a deployed position, as shown by motion arrow 149 in FIG. 18. Additionally, the distal end of prong 144 may be wedged, so that upon contact with the base surface 113 of the aperture 112, prong 144 is encouraged to move outward beyond the shaft 104. Once prong 144 has been deployed, it may provide resistance to screw removal.

FIGS. 17 and 18 depict screw 100 and auxiliary fixation feature 140 operatively assembled in a deployed configuration so that at least a portion of auxiliary fixation feature 140 extends beyond the shaft 104. In the example shown, the extended portion of auxiliary fixation feature 140 is the at least one prong 144 that protrudes at a downward angle from the distal portion of cylindrical cavity 110.

Figure 20:
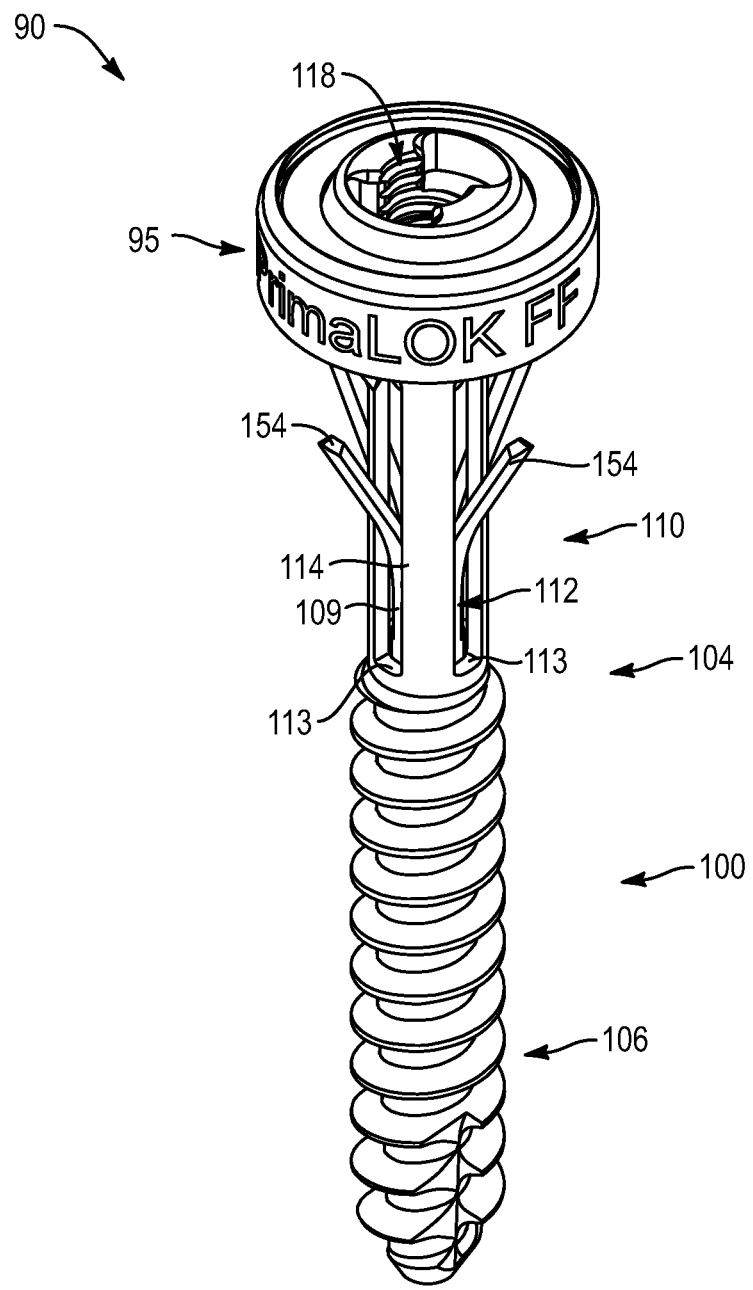
FIG. 20 illustrates a perspective view of the screw system of FIG. 9 with yet another auxiliary fixation feature in a deployed position.
Figure 21:
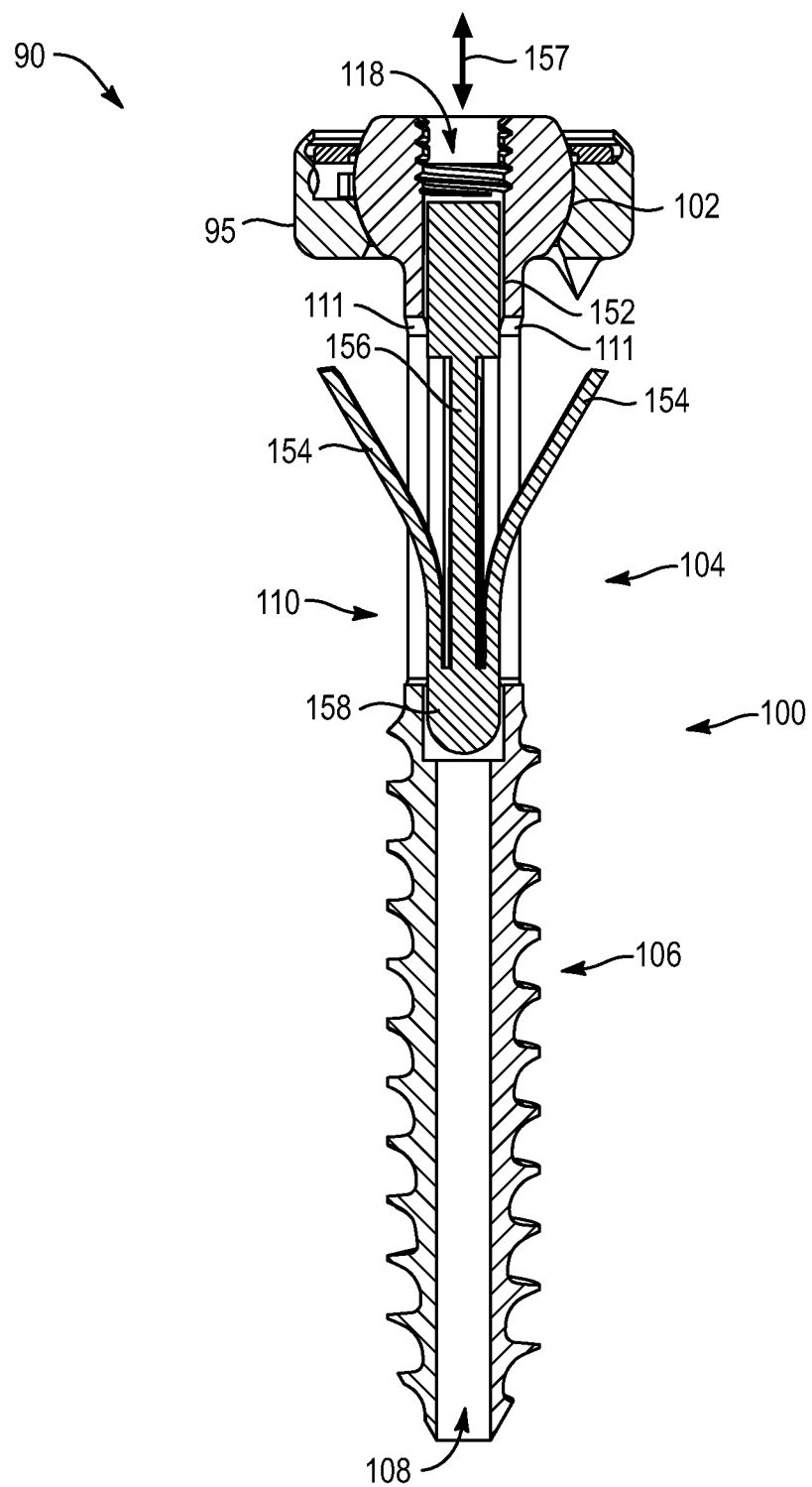
FIG. 21 illustrates a cross section of the screw system and auxiliary fixation feature of FIG. 20.
Figure 22:
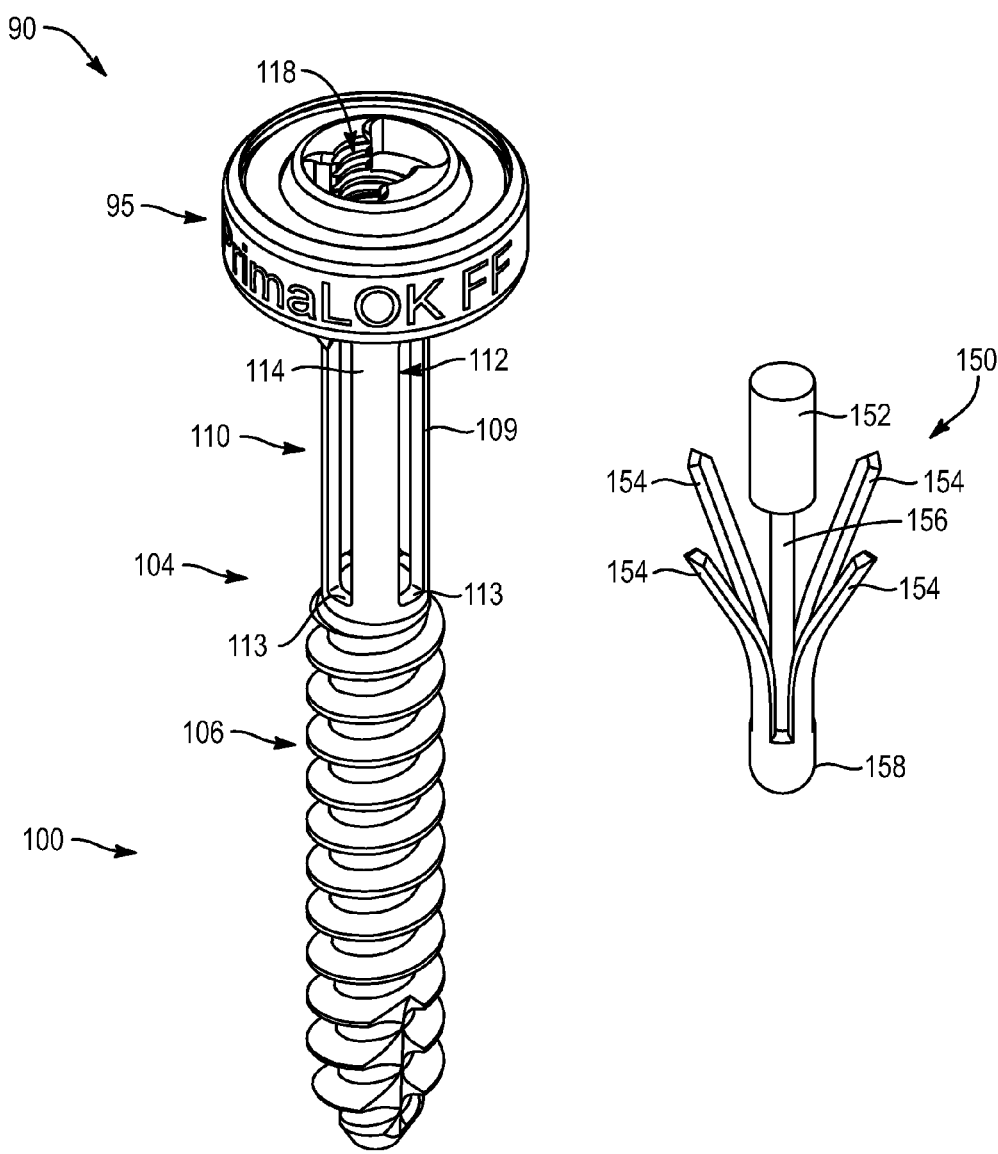
FIG. 22 illustrates an exploded view of the screw system and auxiliary fixation feature of FIG. 20.

FIGS. 20-22 illustrate example of screw 100 and washer 95 with another auxiliary fixation feature 150.

Similar to previously disclosed examples, auxiliary fixation feature 150 is formed separately from screw 100 and can be operatively assembled with screw 100 as seen best in FIGS. 20 and 21. With reference to FIG. 22, auxiliary fixation feature includes a proximal rod 152, a stem 156, a distal base 158, and at least one prong 154. Stem 156 may be positioned between rod 152 and base 158, and may have a smaller radius than the rod 152 or the base 158. The prong 154 may be integral to the base 158 and may extend proximally toward rod 152. For example, FIG. 22 shows four prongs 154 arranged around centrally located stem 156. The prong 154 may have a neutral position parallel to rod 152, or near parallel with a slight bias outward. The rod 152, stem 156, base 158, and prong 154 may all be integrally formed. The maximal diameter of auxiliary fixation feature 152 may be complimentary to the inside diameter of cylindrical cavity 110.

FIGS. 20 and 21 depict screw 100 operatively assembled with the auxiliary fixation feature in a deployed configuration, in which at least a portion of auxiliary fixation feature 150 extends beyond the shaft 104. This example is similar to the previous auxiliary fixation feature 140, in that the protruding portion of the auxiliary fixation feature 150 is at least one prong 154, although it has been inverted to extend from the proximal portion of cylindrical cavity 110.

The auxiliary fixation feature 150 may be operatively assembled with screw 100 through opening 118 into cavity 110. The prong 154, if outwardly biased, may be compressed toward a central longitudinal axis of the auxiliary fixation feature 150 in order to fit into opening 118 and cavity 110. This arrangement of auxiliary fixation feature 150 may be described as an insertion configuration, similar to those described previously. The prong 154 may be intentionally misaligned with the aperture 118 to prevent unintentional protrusion. The auxiliary fixation feature 150 may remain in the insertion position while screw system 90 is inserted, thus providing no resistance to screw insertion.

Once screw system 90 is in place, an axial force 157 may be placed on rod 152 to urge the auxiliary fixation feature 150 to a deployed configuration, in which at least a portion of the auxiliary fixation feature 150 protrudes from the shaft 104. The axial force 157 may be distal or proximal.

A proximal force 157 pulls proximally on the rod 152. As auxiliary fixation feature 150 is pulled proximally, prong 154 may contact the proximal surface 111 of aperture 112 and be forced outwards to a deployed position. To further facilitate the outward motion, the proximal surface of the aperture 112 may be wedged so that prong 154 is guided outward. Additionally, the proximal ends of prong 154 may also be wedged to encourage outward movement into a deployed position, which may provide resistance to screw removal.

In one method of use, the prong 154 may be outwardly biased from rod 152. In the insertion position, the bias may be temporarily overcome so that the prong 154 is parallel or nearly parallel to the rod 152. If auxiliary fixation feature 150 is biased, it may automatically deploy as soon as the prong 154 is aligned with the aperture 112.

Figure 23:
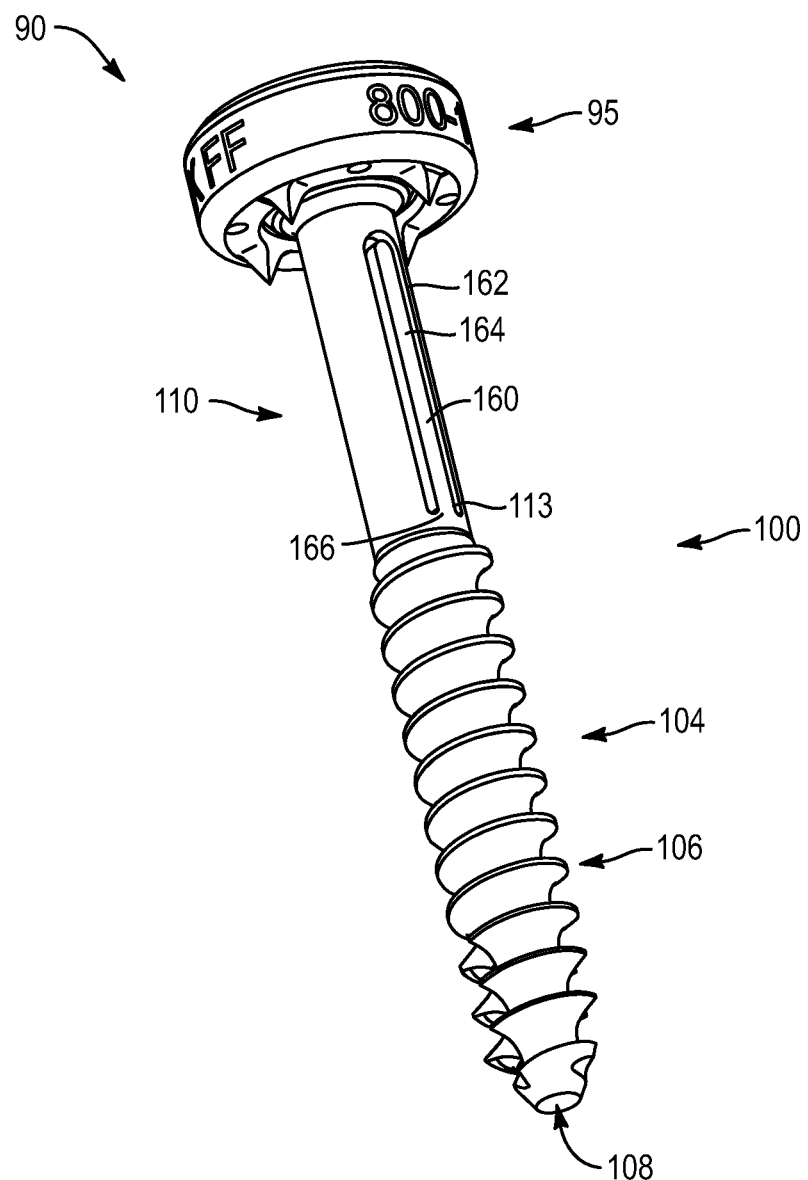
FIG. 23 illustrates a perspective view of the screw system of FIG. 9 with yet another auxiliary fixation feature in an insertion configuration.
Figure 24:
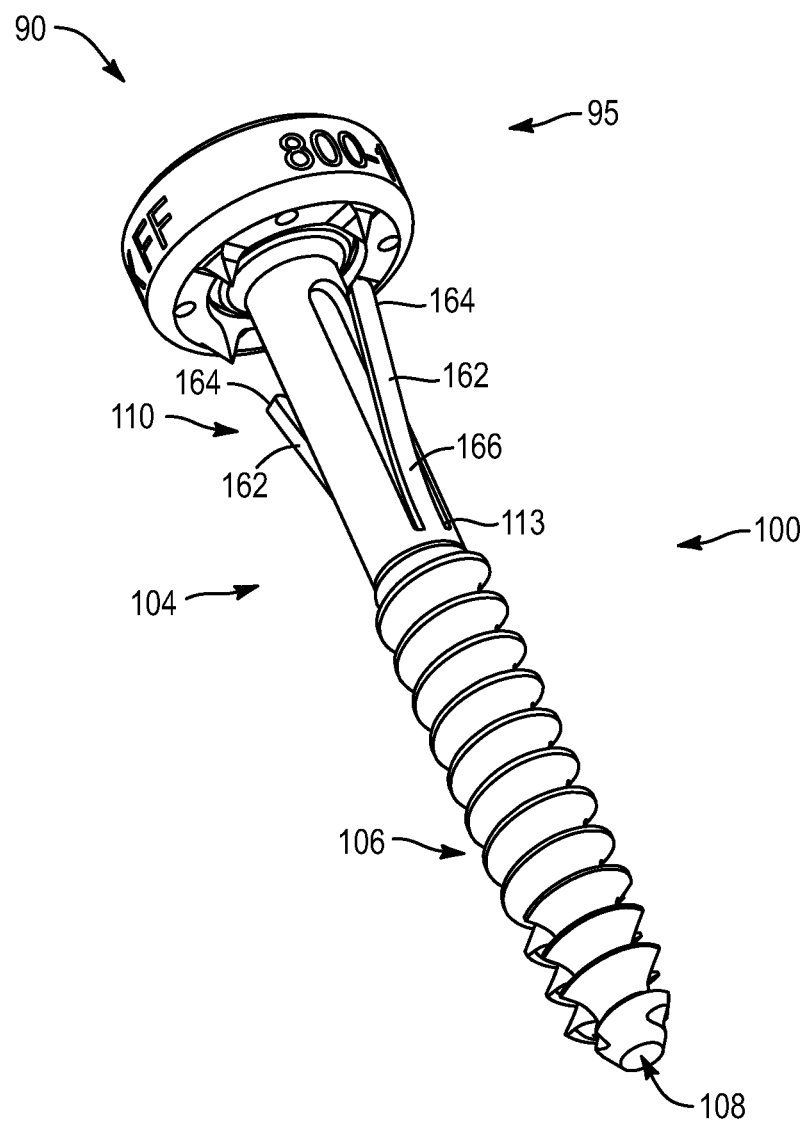
FIG. 24 illustrates a perspective view of the screw system of FIG. 23 with the auxiliary fixation feature in a deployed position.

FIGS. 23-24 illustrate an example of screw 100 and washer 95 with an integral auxiliary fixation device 160. The auxiliary fixation device 160 includes at least one prong 162 that occupies at least a portion of aperture 112. Prong 162 has a proximal free portion 164 and a distal root portion 166 that is connected to the base 113 of aperture 112. The distal connection 166 may also be described as a flexion point where prong 162 can bend outward from the body upon actuation.

FIG. 23 depicts prong 162 in a neutral, insertion position, wherein prong 162 does not protrude significantly from the shaft 104, thus providing no resistance to screw insertion.

FIG. 24 shows prong 162 in a deployed configuration, wherein the proximal free portion 164 extends outward beyond the shaft 104. It can be appreciated in FIG. 24 that the example includes only two apertures 112, oriented opposite one another, unlike the previous examples in which four apertures 112 were depicted.

In one method of use, the prong 162 may be positioned in the insertion configuration during screw insertion. Once screw system 90 is in place, the prong 162 may be actuated using an actuation element, such as an instrument that may be placed into cylindrical cavity 110 and used to push prong 162 outward. The actuation element may also be contained within the shaft 104.

The components of systems 10 and 90 are preferably formed of titanium or titanium alloy. In other embodiments, systems 10 and 90 or any of their component parts may comprise cobalt-chrome and its alloys, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, polymers, or other biocompatible materials. Any part may comprise a combination of any of the materials listed, and the system 10 may comprise parts made of differing materials.

Any of the components disclosed herein may include surface treatments or additives in one or more of the component materials to provide beneficial effects such as anti-microbial, analgesic or anti-inflammatory properties. Any of the components disclosed herein may include coatings or treatments to provide surface roughening, including but not limited to knurling or porous coating, among others. Such treatments may be directionally applied to promote movement between component parts in one direction, and/or increase friction between component parts in another direction.

The present invention may be embodied in other specific forms without departing from its spirit or essential characteristics. It is appreciated that various features of the above described examples and embodiments may be mixed and matched to form a variety of other combinations and alternatives. It is also appreciated that this system should not be limited simply to facet joint fixation. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system, comprising:
   a screw, wherein the screw comprises a spherical head and a shaft extending from the head, wherein the shaft comprises a threaded portion and an auxiliary fixation feature, wherein the threaded portion extends along a distal portion of the shaft,
wherein the system has an insertion configuration and a deployed configuration, wherein the auxiliary fixation feature is substantially contained within the shaft in the insertion configuration, the auxiliary fixation feature comprising a rod, a pin and at least one prong, wherein the pin and the at least one prong extend distally from a distal end of the rod, wherein in the deployed configuration the at least one prong of the auxiliary fixation feature protrudes beyond the shaft and the pin remains within the shaft, wherein the system is transformable between the insertion configuration and the deployed configuration; and
a washer around the head, wherein the washer comprises a socket, wherein the socket receives the head to form a ball-and-socket joint, wherein the screw is freely rotatable relative to the washer when the head rotates in an insertion direction, wherein the screw and washer become locked together when the head rotates in a removal direction, wherein the removal direction is opposite the insertion direction.

2. The system of claim 1, wherein the auxiliary fixation feature is in a non-threaded portion of the shaft proximal to the distal portion.

3. The system of claim 1, wherein the rod comprises a cylindrical center portion, wherein the cylindrical center portion comprises a longitudinal, central axis, wherein each prong extends outwardly from the central axis.

4. The system of claim 3, wherein each prong can protrude beyond the shaft when each prong is aligned with an aperture in the shaft.

5. The system of claim 3, wherein each prong is hinged to the cylindrical center portion.

6. The system of claim 3, wherein each prong is formed separately from the screw.

7. The system of claim 1, wherein the auxiliary fixation feature is spring-biased to protrude beyond the shaft in the deployed configuration, wherein the bias is temporarily overcome in the insertion configuration so that the auxiliary fixation feature is substantially contained within the shaft.

8. A system, comprising:
a fixation element, wherein the fixation element comprises a screw and a washer, wherein the screw comprises a spherical head and a shaft extending from the head, wherein the shaft comprises a distal threaded portion, wherein the washer comprises a socket, wherein the socket receives the head to form a ball-and-socket joint, wherein the screw is freely rotatable relative to the washer when the head rotates in an insertion direction, wherein the screw and washer become locked together when the head rotates in a removal direction thereby locking removal rotation of the screw, wherein the removal direction is opposite the insertion direction; and
an auxiliary fixation element comprising a rod, a pin and at least one prong, wherein the pin and the at least one prong extend distally from a distal end of the rod, wherein the auxiliary fixation element is substantially contained within the fixation element in an insertion configuration, wherein when an axial actuation force is applied, the auxiliary fixation element in a deployed configuration becomes actuated so that the at least one prong protrudes from the fixation element and the pin remains within the fixation element.

9. The system of claim 8, wherein the auxiliary fixation feature is in a non-threaded portion of the shaft proximal to the distal portion.

10. The system of claim 8, wherein the rod comprises a cylindrical center portion, wherein the cylindrical center portion comprises a longitudinal, central axis, wherein each prong extends outwardly from the central axis.

11. The system of claim 10, wherein each prong can protrude beyond the shaft when each prong is aligned with an aperture in the shaft.

12. The system of claim 10, wherein each prong is integrally formed with the cylindrical center portion.

13. The system of claim 8, wherein the auxiliary fixation feature is spring-biased to protrude beyond the shaft in the deployed configuration, wherein the bias is temporarily overcome in the insertion configuration so that the auxiliary fixation feature is substantially contained within the shaft.

14. A bone fastener, comprising:
a fixation element, wherein the fixation element comprises a screw and a washer, wherein the screw comprises a spherical head and a shaft extending from the head, wherein the shaft comprises a distal threaded portion, wherein the washer comprises a socket, wherein the socket receives the head to form a ball-and-socket joint, wherein the screw is freely rotatable relative to the washer when the head rotates in an insertion direction, wherein the screw and washer, when assembled, become locked together and prevents rotation of the screw in a removal direction, wherein the removal direction is opposite the insertion direction; and
an auxiliary fixation element comprising a rod, a pin and at least one prong, wherein the pin and the at least one prong extend distally from a distal end of the rod, wherein the auxiliary fixation element is substantially contained within the shaft of the fixation element during insertion of the fastener, wherein the auxiliary fixation element provides no resistance to insertion of the fastener, wherein the auxiliary fixation element is actuatable after insertion so that the auxiliary fixation element provides resistance to removal of the fastener, wherein when the auxiliary fixation element is actuated the at least one prong protrudes from the shaft and the pin remains within the shaft.

15. The system of claim 14, wherein at least a portion of the auxiliary fixation feature protrudes beyond the shaft after insertion of the fastener.

16. The system of claim 14, wherein the auxiliary fixation feature is in a non-threaded portion of the shaft proximal to the distal portion.

17. The system of claim 14, wherein the rod comprises a cylindrical center portion, wherein the cylindrical center portion comprises a longitudinal, central axis, wherein each prong extends outwardly from the central axis.

18. The system of claim 17, wherein each prong can protrude beyond the shaft when each prong is aligned with an aperture in the shaft.

* * * * *